United States Patent
Donald et al.

(10) Patent No.: US 11,168,309 B2
(45) Date of Patent: *Nov. 9, 2021

(54) URIDINE DIPHOSPHATE-DEPENDENT GLYCOSYLTRANSFERASE ENZYME

(71) Applicant: Manus Bio, Inc., Cambridge, MA (US)

(72) Inventors: Jason Eric Donald, Watertown, MA (US); Ajikumar Parayil Kumaran, Lexington, MA (US); Aaron Love, Boston, MA (US); Christopher Toomey, Cambridge, MA (US); Christine Nicole S. Santos, Newton, MA (US)

(73) Assignee: MANUS BIO INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/912,374

(22) Filed: Jun. 25, 2020

(65) Prior Publication Data
US 2021/0009968 A1    Jan. 14, 2021

Related U.S. Application Data

(60) Provisional application No. 62/866,148, filed on Jun. 25, 2019.

(51) Int. Cl.
*C12N 9/10* (2006.01)
*C12P 19/56* (2006.01)
*C12N 15/52* (2006.01)

(52) U.S. Cl.
CPC ........... *C12N 9/1051* (2013.01); *C12N 15/52* (2013.01); *C12P 19/56* (2013.01)

(58) Field of Classification Search
CPC . C12P 19/56; C12Y 204/01262; C12N 15/52; C12N 9/1051
See application file for complete search history.

(56) References Cited

U.S. PATENT DOCUMENTS 10,273,519 B2 * 4/2019 Broers ................ C12N 9/88
10,463,062 B2 * 11/2019 Philippe .............. A23L 2/60
2013/0171328 A1 7/2013 Kishore et al.
2014/0329281 A1 11/2014 Houghton-Larsen et al.
2017/0332673 A1 11/2017 Philippe et al.
2018/0223264 A1 8/2018 Vroom et al.
2020/0087692 A1 * 3/2020 Kumaran ............... C12P 19/18

FOREIGN PATENT DOCUMENTS

WO    2014122227    8/2014
WO    2016043926    3/2016
WO    2020018506    1/2020

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
International Search Report and Written Opinion for International Application No. PCT/US2020/039648, dated Oct. 9, 2020, 12 pages.

* cited by examiner

*Primary Examiner* — Ganapathirama Raghu
(74) *Attorney, Agent, or Firm* — Morgan, Lewis & Bockius LLP

(57) ABSTRACT

In various aspects, the present invention provides uridine diphosphate-dependent glycosyltransferase (UGT) enzymes capable of catalyzing the transfer of a monosaccharide moiety from a NDP-sugar to the 3' carbon of a sugar moiety of a substrate, such as a terpenoid glycan, thereby functioning as a "1-3 UGT." In other aspects, the invention provides polynucleotides encoding the 1-3 UGT, and host cells comprising the same. In still other aspects, the invention provides methods for preparing glycosylated substrates, including steviol glycosides, using the enzyme and host cells of this disclosure.

26 Claims, 5 Drawing Sheets

Specification includes a Sequence Listing.

FIG. 3A

```
76G1_1(1-306)        MAENKTETTVRRRRRIILFPVPFQGHINPILQLANVLYSKGFSITIFHTNFNKPKTSNYP
MbUGT13_2(156-455)   GSGGSG-----RRRRIILFPVPFQGHINPMLQLANVLYSKGFSITIFHTNFNKPKTSNYP
                     : ..       ************** *********************************

76G1_1(1-306)        HFTFRFILDNDPQDERISNLPTHGPLAGMRIPIINEHGADELRRELELLMLASEEDEEVS
MbUGT13_2(156-455)   HFTFRFILDNDPQDERISNLPTHGPLAGMRIPIINEHGADELRRELELQMLASEEDEEVS
                     ************************************************ **********

76G1_1(1-306)        CLITDALWYFAQSVADSLNLRRLVLMTSSLFNFHAHVSLPQFDELGYLDPDDKTRLEEQA
MbUGT13_2(156-455)   CLITDALWYFAQSVADSLNLPRLVLMTSSLFNFHAHVSLPQFDELGYLDPDDKTRLEEQA
                     ******************** ***************************************

76G1_1(1-306)        SGFPMLKVKDIKSAYSNWQIAKEILGKMIKQTKASSGVIWNSFKELEESELETVIREIPA
MbUGT13_2(156-455)   SGFPMLKVKDIKSAYSNWQIAKEILGKMIKQTKASSGVIWNSFKELEESELETVIREIPA
                     ************************************************************

76G1_1(1-306)        PSFLIPLPKHLTASSSSLLDHDRTVFQWLDQQPPSSVLYVSFGSTSEVDEKDFLEIARGL
MbUGT13_2(156-455)   PSFLIPLPKHLTASSSSLLEHDRTVFQWLDQQPPSSVLYVSFGSTSEVDEKDFLEIARGL
                     ******************* ****************************************

76G1_1(1-306)        VDSKQS
MbUGT13_2(156-455)   VDSQS-
                     ***:.
```

FIG. 3B

```
76G1_1(307-459)      --FLWVVRPGFVKGSTWVEPLPDGFLGERGRIVKWVPQQEVLAHGAIGAFWTHSGWNSTL
MbUGT13_2(1-155)     MAFLWVVRPGFVKGSTWVEPLPDGFLGERGRIVKWVPQQEVLAHGAIGAFWTHGGWNSTL
                       *************************************************.******

76G1_1(307-459)      ESVCEGVPMIFSDFGLDQPLNARYMSDVLKVGVYLENGWERGEIANAIRRVMVDEEGEYI
MbUGT13_2(1-155)     ESVCEGVPMIFSDFGLDQPLNARYMSDVLKVGVYLENGWERGEIANAIRRLMVDEEGEYI
                     **************************************************:********

76G1_1(307-459)      RQNARVLKQKADVSLMKGGSSYESLESLVSYISSL
MbUGT13_2(1-155)     RQNARVLKQKADVSLMKGGSSYESLESLVSYISSL
                     ***********************************
```

URIDINE DIPHOSPHATE-DEPENDENT GLYCOSYLTRANSFERASE ENZYME

RELATED APPLICATIONS

This application claims the benefit of U.S. Provisional Patent Application No. 62/866,148, filed Jun. 25, 2019, the entire disclosure of which is hereby incorporated by reference in its entirety.

TECHNICAL FIELD

The present disclosure relates to enzymes, encoding polynucleotides, host cells, and methods for producing glycosylated substrates.

DESCRIPTION OF THE TEXT FILE SUBMITTED ELECTRONICALLY

The contents of the text file submitted electronically herewith are incorporated herein by reference in their entirety: a computer readable format copy of the Sequence Listing (filename: MAN-024PC_Sequence Listing_ST25.txt; date recorded: Jun. 24, 2020; file size: 28,457 bytes).

BACKGROUND

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling their intake of carbohydrates.

Steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in Stevia leaves, composing approximately 10% to 20% of the total dry weight. On a dry weight basis, the four major glycosides found in the leaves of Stevia typically include stevioside (9.1%), Rebaudioside A (3.8%), Rebaudioside C (0.6-1.0%) and dulcoside A (0.3%). Other known steviol glycosides include Rebaudiosides B, C, D, E, F and M, steviolbioside and rubusoside.

The minor glycosylation product Rebaudioside M (RebM) is estimated to be about 200-350 times more potent than sucrose, and is described as possessing a clean, sweet taste with a slightly bitter or licorice aftertaste. Prakash I. et al., Development of Next Generation Stevia Sweetener: Rebaudioside M, *Foods* 3(1), 162-175 (2014). Reb M is of great interest to the global food industry.

Processes for preparing steviol glycosides from the stevia plant are not sustainable, and are not suitable for providing the minor glycosylation products of stevia leaves. Accordingly, there remains a need for sustainable and economical methods for preparing compositions comprising steviol glycosides, including highly purified steviol glycoside compositions. Further, methods are needed for producing substantial amounts of the minor glycosylation products, such as RebM, and others.

SUMMARY OF THE INVENTION

In various aspects, the present invention provides uridine diphosphate (UDP)-dependent glycosyltransferase (UGT) enzymes capable of catalyzing the transfer of a monosaccharide moiety from an NDP-sugar (e.g., UDP-sugar) to the 3' carbon of a sugar moiety of a substrate, such as a terpenoid glycan, thereby functioning as a "1-3 UGT." In other aspects, the invention provides polynucleotides encoding the 1-3 UGT, and host cells comprising the same. In still other aspects, the invention provides methods for preparing glycosylated substrates, including steviol glycosides, using the enzyme and host cells of this disclosure.

The 1-3 UGT exhibits high glycosyltransferase activity on terpenoid glycosides, such as steviol glycosides. For example, the 1-3 UGT catalyzes transfer of a monosaccharide moiety from an NDP-sugar to the 3' carbon of a sugar moiety on a terpenoid glycan, such as stevioside and RebD. That is, where the substrate is a steviol glycoside, the 1-3 UGT can catalyze NDP-dependent transfer of a monosaccharide moiety to the 3' carbon of both the C13- or C19-linked glucose moieties. In various embodiments, the 1-3 UGT catalyzes the biosynthesis of RebM.

In one aspect, the invention provides a 1-3 UGT enzyme comprising an amino acid sequence that is at least about 75% identical to the amino acid sequence of SEQ ID NO: 5 or SEQ ID NO: 6. In some embodiments, the enzyme comprises an amino acid substitution at positions corresponding to positions 29, 200, 357, and 414 of SEQ ID NO: 1 (*Stevia rebaudiana* UGT76G1). Substitutions at these positions, which are included in the enzyme of SEQ ID NOS: 5 and 6 (positions 183, 354, 54, and 111, respectfully, in SEQ ID NO: 5) can provide dramatic improvements in activity relative to the enzyme of SEQ ID NO: 1.

In some embodiments, the 1-3 UGT enzyme comprises an insertion (with respect to SEQ ID NO: 1) of from 5 to about 15 amino acids, or about 6 to about 12 amino acids, after the position corresponding to position 155 of SEQ ID NO: 5. In some embodiments, the insertion is a flexible and hydrophilic sequence, which may be predominately Glycine and Serine residues. In some embodiments, the sequence is GSGGSG (SEQ ID NO: 7) or GSGGSGGSG (SEQ ID NO: 8).

In various embodiments, the 1-3 UGT enzyme shows improved conversion of stevioside to Reb A, and improved conversion of RebD to RebM, as compared to UGT76G1-L200A (SEQ ID NO: 3).

In some embodiments, the identity of amino acids at positions corresponding to positions 183, 354, 54, and 111 of SEQ ID NO: 5, allows for further modification at other positions. For example, in some embodiments, the 1-3 UGT enzyme comprises an amino acid sequence that is at least about 60% identical to the amino acid sequence of SEQ ID NO: 5, wherein the UGT enzyme comprises: a glycine (G) or threonine (T) at the position corresponding to position 54 of SEQ ID NO: 5; a leucine (L) or isoleucine (I) at the position corresponding to position 111 of SEQ ID NO: 5; a methionine (M) or leucine (L) at the position corresponding to position 183 of SEQ ID NO: 5; and an alanine (A), or glycine (G), or serine (S) at the position corresponding to position 354 of SEQ ID NO: 5. In some embodiments, the 1-3 UGT enzyme comprises a methionine (M) at the position corresponding to position 183 of SEQ ID NO: 5. In some embodiments, the 1-3 UGT enzyme comprises a glycine (G) at the position corresponding to position 54 of SEQ ID NO: 5. In some embodiments, the 1-3 UGT enzyme comprises a leucine (L) at the position corresponding to position 111 of SEQ ID NO: 5. In some embodiments, the 1-3 UGT has two or three of a methionine (M) at the position corresponding to position 183 of SEQ ID NO: 5, a glycine (G) at the position corresponding to position 54 of SEQ ID NO: 5, and a leucine (L) at the position corresponding to position 111 of SEQ ID NO: 5. These modifications can provide substantial improvements to the activity of the enzyme, relative to the amino acid identity at the corresponding position of SEQ ID NO: 1.

In some embodiments, the 1-3 UGT enzyme includes one or more of: a deletion of amino residues 159 to 161 with reference to the amino acid sequence of SEQ ID NO: 5, a substitution at position 262 (e.g., L262Q), a substitution at position 294 (e.g., R294), and a substitution at position 413 (e.g., D413E), in each case with reference to the amino acid sequence of SEQ ID NO: 5.

In embodiments, the 1-3 UGT enzyme includes a deletion of amino residues 159 to 161 as well as the amino acid substitutions L262Q, R294P and D413E, each with reference to the amino acid sequence of SEQ ID NO: 5. An exemplary UGT enzyme according to these embodiments is disclosed herein as SEQ ID NO: 6).

In some embodiments, the 1-3 UGT enzyme includes a deletion of residues of one or more of residues E225 to T232 with reference to the amino acid sequence of SEQ ID NO: 6. In these or other embodiments, the 1-3 UGT enzyme includes one or more amino acid substitutions at positions selected from position 72 (e.g., S72Q), position 305 (e.g., A305C), position 345 (e.g., Y345F), and position 428 (e.g., L428I), in each case with reference to the amino acid sequence of SEQ ID NO: 6. In exemplary embodiments, the 1-3 UGT enzyme includes a deletion of amino residues E225 to T232 as well as the amino acid substitutions S72Q, A305C, Y345F, and L428I, in each case with reference to the amino acid sequence of SEQ ID NO: 6. An exemplary UGT enzyme in accordance with these embodiments is disclosed herein as SEQ ID NO: 9).

In some embodiments, the amino acid modifications described herein are alternatively applied to SrUGT76G1, or circular permutants thereof.

In other aspects, the invention provides polynucleotides encoding the 1-3 UGT enzyme disclosed herein, as well as host cells comprising the same. The host cell may be a microorganism, a fungal cell, an algal cell, or a plant cell. The plant may be a stevia plant or, more particularly, a *Stevia rebaudiana* plant. Stevia plants naturally express the enzymes required to synthesize steviol and steviol glycosides, but they produce only trace amounts of highly glycosylated steviol glycosides such as RebM. In contrast, the RebM content of a stevia or *Stevia rebaudiana* plant expressing a polynucleotide encoding the 1-3 UGT may produce comparatively high levels of RebA, RebD, and/or RebM; or other typically minor steviol glycosides comprising a 1-3 glycosylation such as RebB, RebG, RebI, and Reb4. In various embodiments, the cell is a microbial cell, such as *E. coli*.

In the various embodiments, the host cell may express one or more additional UGT enzymes selected from C-13 UGT enzyme, a C-19 UGT enzyme, and a 1-2 UGT enzyme. "C-13 UGT" or UGTc13 is a glycosyltransferase capable of glycosylating steviol or a steviol glycoside at its C13 hydroxyl group. "C-19 UGT" or UGTc19 is a glycosyltransferase capable of glycosylating steviol or a steviol glycoside at its C19 carboxyl group. "1-2 UGT" or UGT1-2 is a glycosyltransferase capable of β1,2 glycosylation of the C2' of a 13-O-glucose, and/or a 19-O-glucose. "1-3 UGT" or UGT1-3 is a glycosyltransferase capable of β1,3 glycosylation of the C3' of a 13-O-glucose, and/or a 19-O-glucose.

In some embodiments, the host cell expresses (in addition to the 1-3 UGT enzyme) a heterologous C-13 UGT enzyme, a heterologous C-19 UGT enzyme, and a heterologous 1-2 UGT enzyme, and is thus capable of glycosylating steviol and steviol glycoside substrates to produce RebM.

In some embodiments, the host cell (e.g., bacterial or yeast cell) produces steviol substrate by expression of endogenous and/or heterologous enzymes for biosynthesis of steviol. In these embodiments, the cell produces steviol glycosides, such as RebM, from carbon sources such as glucose, sucrose, or glycerol, among others.

In some aspects, the invention provides a method for transferring a monosaccharide group to a substrate. The method comprises contacting an NDP-sugar (e.g., UDP-monosaccharide) and the substrate with the 1-3 UGT enzyme described herein, or with a host cell expressing the 1-3 UGT enzyme or a lysate thereof. Various substrates can be glycosylated according to this disclosure, including but not limited to terpenoids. In some embodiments, the substrate is a terpenoid substrate, and can be a diterpenoid, such as steviol and/or steviol glycosides. In some embodiments, the substrate comprises stevioside and/or RebD. In various embodiments, the nucleotide diphosphate is UDP or ADP, or other NDP capable of acting as a glycosyl donor molecule. In various embodiments, the monosaccharide is glucose, galactose, fructose, rhamnose, or xylose. In some embodiments, the monosaccharide is glucose. The NDP-sugar can be supplied exogenously for in vitro reactions, or is produced endogenously by a host cell for embodiments that employ microbial fermentation or biotransformation reactions. Various modifications can be made to the host cell to increase available UDP-glucose to support the reactions.

In some embodiments, the substrate comprises a plant extract, which is optionally a stevia leaf extract. In various embodiments, a microbial cell expressing the 1-3 UGT may be fed with steviol or a lower order steviol glycoside for the production of higher order steviol glycosides, including RebD and RebM. Advanced intermediates from stevia leaf extract are readily available from existing industrial extraction of steviol glycosides.

In various embodiments, the 1-3 UGT converts a lower order steviol glycoside to a higher order steviol glycoside. For example, the UGT enzyme may have 1-3' UGT activity for the conversion of steviobioside to RebB, rubusoside to RebG, stevioside to Reb A, Reb A to RebI, RebG to Reb4, RebE to Reb D, and/or Reb D to Reb M. Alternatively, the UGT may be used in combination with another 1-3 UGT enzyme or enzymes having a preference of specificity for certain substrates. For example, one UGT may preferentially act as a 1-3 UGT on C13 glycosyl substrates whereas another UGT enzyme preferentially acts as a 1-3 UGT on C19 glycosyl substrates.

In some embodiments, the method comprises growing the host cell in the presence of the substrate. The substrate may be fed to the culture, or in some embodiments, the substrate is synthesized by the host cell. In some embodiments, the substrate comprises steviol or comprises a mixture of stevioside and RebA as major components, and the host cell expresses a plurality of UGT enzymes to produce target steviol glycosides, such as RebM.

DESCRIPTION OF THE FIGURES

FIG. 3A-FIG. 3B show amino acid sequence alignment of SrUGT76G1 (SEQ ID NO: 1) and MbUGT1-3_2 (SEQ ID NO: 6), which is a circularly permuted version of SrUGT76G1. FIG. 3A shows the N-terminal portion of SrUGT76G1 aligned to the C-terminal portion of MbUGT1-3_2. FIG. 3B shows the C-terminal portion of SrUGT76G1 aligned to the N-terminal portion of MbUGT1-3_2.

DETAILED DESCRIPTION OF THE INVENTION

In various aspects, the present invention provides uridine diphosphate-dependent glycosyltransferase (UGT) enzymes capable of catalyzing the transfer of a monosaccharide moiety from an NDP-sugar (e.g., UGT-glucose) to the 3' carbon of a sugar moiety of a substrate, such as a terpenoid glycan, thereby functioning as a "1-3 UGT." In other aspects, the invention provides polynucleotides encoding the 1-3 UGT, and host cells comprising the same. In still other aspects, the invention provides methods for preparing glycosylated substrates, including steviol glycosides, using the enzyme and host cells of this disclosure.

The 1-3 UGT enzyme exhibits high glycosyltransferase activity on terpenoid glycosides, such as steviol glycosides. For example, the 1-3 UGT enzyme catalyzes transfer of a monosaccharide moiety from an NDP-sugar to the 3' carbon of a sugar moiety on a terpenoid glycan, such as stevioside and RebD. That is, where the substrate is a steviol glycoside, the 1-3 UGT can catalyze NDP-dependent transfer of a monosaccharide moiety to the 3' carbon of both the C13- or C19-linked sugar (e.g., glucose) moieties. In some embodiments, the 1-3 UGT enzyme has a higher rate or productivity for glycosylation at the C19-linked sugar, as compared to at the C13-linked sugar. In some embodiments, the monosaccharide is glucose, but in other embodiments, the monosaccharide may be galactose, fructose, rhamnose, xylose, or other monosaccharide.

Figure 1:
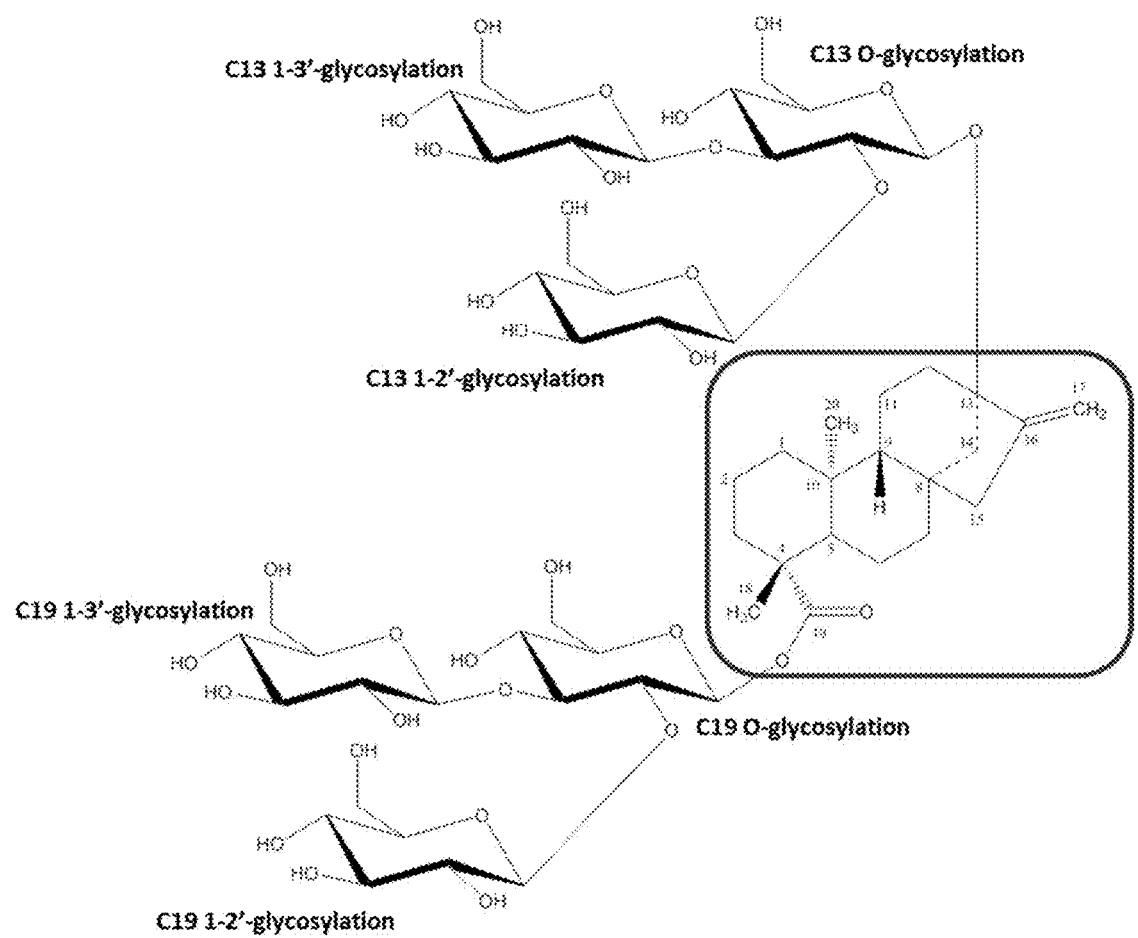
FIG. 1 shows the chemical structure of Rebaudioside M (RebM), a minor component of the steviol glycoside family. RebM is a derivative of the diterpenoid steviol (box) with six glucosyl modifications.
Figure 2:
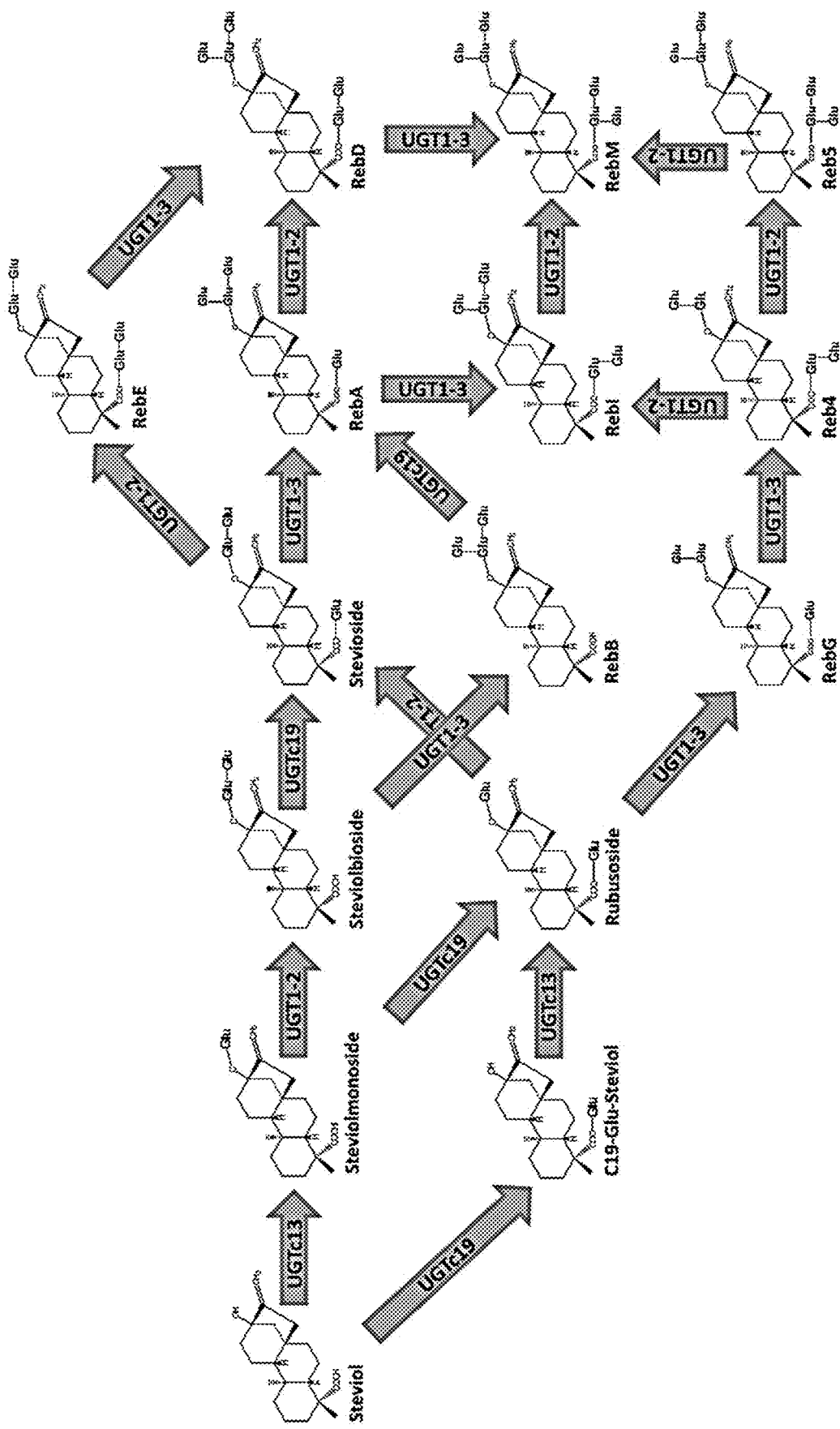
FIG. 2 shows glycosylation pathways from steviol to RebM and other steviol glycosides. UGTc13 is a glycosyltransferase capable of glycosylating steviol or a steviol glycoside at its C13 hydroxyl group. UGTc19 is a glycosyltransferase capable of glycosylating steviol or a steviol glycoside at its C19 carboxyl group. UGT1-2 is a glycosyltransferase capable of β1,2 glycosylation of the C2' of a 13-O-glucose, and/or a 19-O-glucose. UGT1-3 is a glycosyltransferase capable of β1,3 glycosylation of the C3' of a 13-O-glucose, and/or a 19-O-glucose.

In various embodiments, the 1-3 UGT catalyzes the biosynthesis of RebM. The structure of RebM is shown in FIG. 1. RebM comprises a steviol scaffold with six glycosylations: (1) a C13 O-glycosylation, (2) a C13 1-2 glycosylation, (3) a C13 1-3 glycosylation, (4) a C19 O-glycosylation, (5) a C19 1-2 glycosylation, and (6) a C19 1-3 glycosylation. As shown in FIG. 2, the 1-3 UGT can produce RebM through the transfer of an additional glucose to RebD substrate. Further, the 1-3 UGT enzyme can catalyze the transfer of a monosaccharide to other steviol glycoside substrates, producing products such as RebB (from steviolbioside), RebG (from rubusoside), Reb4 (from RebG), RebA (from stevioside), RebD (from RebE), and RebI (from RebA). In some embodiments, the substrate comprises a plant extract, such as a stevia leaf extract, and the 1-3 UGT (along with the action of other glycosyltransferase enzymes) is able to glycosylate the various major or minor glycosylation products to produce a product that is predominately RebM.

In one aspect, the invention provides a 1-3 UGT enzyme comprising an amino acid sequence that is at least about 75% identical to the amino acid sequence of SEQ ID NO: 5 or SEQ ID NO: 6. In some embodiments, the 1-3 UGT comprises an amino acid sequence that is at least about 80% identical to SEQ ID NO: 5 or 6. In some embodiments, the amino acid sequence is at least about 85% identical to SEQ ID NO: 5 or 6, or at least about 90% identical to SEQ ID NO: 5 or 6, or at least about 95% identical to SEQ ID NO: 5 or 6, or at least about 98% identical to SEQ ID NO: 5 or 6. In some embodiments, the amino acid sequence comprises the amino acid of SEQ ID NO: 5 or 6.

In some embodiments, the 1-3 UGT enzyme comprises an amino acid sequence that is at least about 75% identical to the amino acid sequence of SEQ ID NO: 9. In some embodiments, the 1-3 UGT comprises an amino acid sequence that is at least about 80% identical to SEQ ID NO: 9. In some embodiments, the amino acid sequence is at least about 85% identical to SEQ ID NO: 9, or at least about 90% identical to SEQ ID NO: 9, or at least about 95% identical to SEQ ID NO: 9, or at least about 98% identical to SEQ ID NO: 9. In some embodiments, the amino acid sequence comprises the amino acid of SEQ ID NO: 9.

For example, the amino acid sequence may have from 1 to 20 amino acid modifications independently selected from substitutions, deletions, and insertions, with respect to the amino acid sequence SEQ ID NO: 5 or 6. In some embodiments, the amino acid sequence has from 1 to 10 amino acid modifications (e.g., from 1 to 5) independently selected from substitutions, deletions, and insertions, with respect to the amino acid sequence of SEQ ID NO: 5 or 6. In some embodiments, the UGT amino acid sequence has from 1 to 20 amino acid modifications independently selected from substitutions, deletions, and insertions, with respect to the amino acid sequence of SEQ ID NO: 9. In some embodiments, the amino acid sequence has from 1 to 10 amino acid modifications (e.g., from 1 to 5) independently selected from substitutions, deletions, and insertions, with respect to the amino acid sequence of SEQ ID NO: 9. Amino acid modifications to the amino acid sequence of SEQ ID NO: 5, 6, or 9, can be guided by available enzyme structures and construction of homology models. Exemplary structures are described in, e.g., Li, et al., "Crystal Structure of Medicago truncatula UGT85H2—insights into the Structural Basis of a Multifunctional (iso) Flavonoid Glycosyltransferase," *J. of Mol. Biol.* 370.5 (2007): 951-963 as well as Lee et al., "Molecular Basis for Branched Steviol Glucoside Biosynthesis," *PNAS* 116:13131-13136 (2019). Publicly available crystal structures (e.g., PDB entry: 2PQ6) may be used to inform amino acid modifications. For example, one or more amino acid modifications can be made to the active site or in the vicinity of the active site to improve the binding of substrate, and/or to improve reaction geometries of these substrates with catalytic side chains.

In some embodiments, the enzyme comprises an amino acid substitution at positions corresponding to positions 29, 200, 357, and 414 of SEQ ID NO: 1 (*Stevia rebaudiana* UGT76G1). Substitutions at these positions, which are included in the enzyme of SEQ ID NOS: 5, 6, and 9 (positions 183, 354, 54, and 111, respectfully, in SEQ ID NO: 5) can provide dramatic improvements in activity. In some embodiments, the identity of amino acids at positions corresponding to positions 183, 354, 54, and 111 of SEQ ID NO: 5, allows for further modification at other positions. For example, in some embodiments, the 1-3 UGT enzyme comprises an amino acid sequence that is at least about 60% identical to the amino acid sequence of SEQ ID NO: 5, 6, or 9, wherein the UGT enzyme comprises: a glycine (G) or threonine (T) at the position corresponding to position 54 of SEQ ID NO: 5; a leucine (L) or isoleucine (I) at the position corresponding to position 111 of SEQ ID NO: 5; a methionine (M) or leucine (L) at the position corresponding to position 183 of SEQ ID NO: 5; and an alanine (A), or glycine (G), or serine (S) at the position corresponding to position 354 of SEQ ID NO: 5. In some embodiments, the 1-3 UGT enzyme comprises a methionine (M) at the position corresponding to position 183 of SEQ ID NO: 5. In some embodiments, the 1-3 UGT enzyme comprises a glycine (G) at the position corresponding to position 54 of SEQ ID NO: 5. In some embodiments, the 1-3 UGT enzyme comprises a leucine (L) at the position corresponding to position 111 of SEQ ID NO: 5. In some embodiments, the 1-3 UGT has two or three of a methionine (M) at the position corresponding to position 183 of SEQ ID NO: 5, a glycine (G) at the position corresponding to position 54 of SEQ ID NO: 5, and a leucine (L) at the position corresponding to position 111 of SEQ ID NO: 5. These modifications can provide substantial improvements to the activity of the enzyme.

The 1-3 UGT enzyme may comprise other substitutions at the position corresponding to position 54 of SEQ ID NO: 5, other than Serine, which is at the corresponding position (357) of SEQ ID NO: 1. Thus, in some embodiments, the substitution at the position corresponding to position 54 of SEQ ID NO: 5 is a hydrophobic amino acid, such as alanine (A), valine (V), leucine (L), isoleucine (I), phenylalanine (F), or methionine (M). In some embodiments, the amino acid at the position corresponding to position 54 of SEQ ID NO: 5 has a side chain that does not have the ability to provide a hydrogen bond. In other embodiments, the amino acid at the position corresponding to position 54 of SEQ ID NO: 5 is Glycine (G), asparagine (N), cysteine (C), glutamine (Q), threonine (T), or tyrosine (Y).

In various embodiments, the 1-3 UGT enzyme comprises a leucine (L) amino acid at the position corresponding to position 111 of SEQ ID NO: 5. In some embodiments, the 1-3 UGT enzyme may comprise an amino acid other than leucine at this position. In various embodiments, the position corresponding to position 111 of SEQ ID NO: 5 will not be Valine, the amino acid at the corresponding position of SEQ ID NO: 1. Other suitable substitutions at the position corresponding to position 111 may include glycine (G), alanine (A), isoleucine (I) or methionine (M). In some embodiments, the amino acid at the position corresponding to position 111 of SEQ ID NO: 5 has a side chain that is less hydrophobic and/or bulky than valine.

In various embodiments, the UGT comprises a methionine (M) amino acid at the position corresponding to position 183 of SEQ ID NO: 5. In various embodiments, the UGT comprises another suitable amino acid at this position, other than isoleucine, which is at the corresponding position of SEQ ID NO: 1. For example, the amino acid at this position may have a side chain that is less hydrophobic than isoleucine and/or may provide a hydrogen bond. Some exemplary substitutions at the position corresponding to position 183 of SEQ ID NO: 5 include alanine (A), valine (V), leucine (L), Cysteine (C), Serine (S), Threonine (T), Tyrosine (Y), Asparagine (N), Glutamine (Q), Aspartic Acid (D), and Glutamic acid (E).

In various embodiments, the 1-3 UGT comprises an Alanine (A) or Glycine (G) at the position corresponding to position 354 of SEQ ID NO: 5. In various embodiments, the amino acid at this position has a side chain that is less hydrophobic and/or less bulky than leucine, which is at the corresponding position of SEQ ID NO: 1.

In some embodiments, the 1-3 UGT enzyme comprises an insertion (with respect to UGT76G1, SEQ ID NO: 1) of from 5 to about 15 amino acids, such as from 6 to 12 amino acids, or about 6 or about 11 amino acids, after the position corresponding to position 155 of SEQ ID NO: 5. In some embodiments, the insertion is a flexible and hydrophilic sequence, that is predominately Glycine and Serine residues. In some embodiments, the sequence is GSGGSG (SEQ ID NO: 7) or GSGGSGGSG (SEQ ID NO: 8).

In various embodiments, the 1-3 UGT enzyme shows improved conversion of stevioside to Reb A, and improved conversion of RebD to RebM, as compared to UGT76G1-L200A (SEQ ID NO: 3). This improved conversion is exhibited in a bioconversion assay where stevioside or RebD substrate is fed to microbial cells expressing the 1-3 UGT enzyme of this disclosure. Improved conversion can be demonstrated in reactions with cell lysates containing recombinantly expressed 1-3 UGT, or in vitro reactions with purified or partially purified 1-3 UGT. Such reactions are well known in the art. Alternatively, whole cell assays can be used. For example, an E. coli strain (ΔushA, ΔgalETKM, Δpgi; overexpressed pgm, galU) expressing the 1-3 UGT enzyme is grown overnight in 96-well plates at 250 rpm at 37° C. The cells are then transferred to a fresh production culture to 10% of the total volume. 0.5 mM substrate (e.g., stevioside or Rebaudioside D) are included in the production culture. The production culture is then grown for 48 hours in 96-well plates at 250 rpm at 37° C. Products can be quantified using a LC-MS QQQ.

In some embodiments, the identity of amino acids at positions corresponding to positions 183, 354, 54, and 111 of SEQ ID NO: 5, allows for further modification at other positions. For example, in some embodiments, the 1-3 UGT enzyme comprises an amino acid sequence that is at least about 60% identical to the amino acid sequence of SEQ ID NO: 5, 6, or 9, wherein the UGT enzyme comprises: a glycine (G) or threonine (T) at the position corresponding to position 54 of SEQ ID NO: 5; a leucine (L) or isoleucine (I) at the position corresponding to position 111 of SEQ ID NO: 5; a methionine (M) or leucine (L) at the position corresponding to position 183 of SEQ ID NO: 5; and an alanine (A), or glycine (G), or serine (S) at the position corresponding to position 354 of SEQ ID NO: 5. In some embodiments, the 1-3 UGT enzyme comprises a methionine (M) at the position corresponding to position 183 of SEQ ID NO: 5. In some embodiments, the 1-3 UGT enzyme comprises a glycine (G) at the position corresponding to position 54 of SEQ ID NO: 5. In some embodiments, the 1-3 UGT enzyme comprises a leucine (L) at the position corresponding to position 111 of SEQ ID NO: 5. In some embodiments, the 1-3 UGT has two or three of a methionine (M) at the position corresponding to position 183 of SEQ ID NO: 5, a glycine (G) at the position corresponding to position 54 of SEQ ID NO: 5, and a leucine (L) at the position corresponding to position 111 of SEQ ID NO: 5. These modifications can provide substantial improvements to the activity of the enzyme. In some embodiments, the amino acid sequence is at least about 70% identical to the amino acid sequence of SEQ ID NO: 5, 6, or 9, or at least about 80% identical to the amino acid sequence of SEQ ID NO: 5, 6, or 9, or at least about 90% identical to the amino acid sequence of SEQ ID NO: 5, 6, or 9, or at least about 95% to the amino acid sequence of SEQ ID NO: 5, 6, or 9.

In some embodiments, the 1-3 UGT enzyme comprises a glycine (G) amino acid at the position corresponding to position 54 of SEQ ID NO: 5, a leucine (L) amino acid at the position corresponding to position 111 of SEQ ID NO: 5; and a methionine (M) amino acid at the position corresponding to position 183 of SEQ ID NO: 5.

In some embodiments, the 1-3 UGT enzyme comprises a glycine (G) amino acid at the position corresponding to position 54 of SEQ ID NO: 5, and a leucine (L) amino acid at the position corresponding to position 111 of SEQ ID NO: 5.

In some embodiments, the 1-3 UGT enzyme comprises a glycine (G) amino acid at the position corresponding to position 54 of SEQ ID NO: 5, and a methionine (M) amino acid at the position corresponding to position 183 of SEQ ID NO: 5.

In some embodiments, the 1-3 UGT enzyme comprises a leucine (L) amino acid at the position corresponding to position 111 of SEQ ID NO: 5 and a methionine (M) amino acid at the position corresponding to position 183 of SEQ ID NO: 5.

In these or other embodiments, the 1-3 UGT enzyme has a deletion of one or more amino acids at positions E225 to T232, with respect to the amino acid sequence of SEQ ID NO: 6. For example, the UGT may have a deletion of at least two, at least three, at least four, at least five, at least six, at least seven, or eight amino acids corresponding to amino acids E225-T232 of SEQ ID NO: 6.

In these or other embodiments, the 1-3 UGT enzyme further includes one or more of amino acid substitutions at positions corresponding to position 72, position 305, position 345, and position 428. For example, 1-3 UGT enzyme may have a substitution of glutamine (Q) or asparagine (N) at the position corresponding to position 72 of SEQ ID NO: 6. In some embodiments, the 1-3 UGT enzyme has a substitution of a neutral hydrophilic amino acid, such as cysteine (C), Serine (S), or Threonine (T) at the position corresponding to position 305 of SEQ ID NO: 6. In some embodiments, the 1-3 UGT enzyme has a substitution of phenylalanine (F) or Tryptophan (W) at the position corresponding to position 345 of SEQ ID NO: 6. In some embodiments, the 1-3 UGT enzyme has a substitution of isoleucine (I), valine (V), or alanine (A) at the position corresponding to position 428 of SEQ ID NO: 6. In some embodiments, the 1-3 UGT enzyme has 2, 3, or 4 of the following substitutions with respect to SEQ ID NO: 6: S72Q, A305C, Y345F, and L428I.

In some embodiments, the 1-3 UGT enzyme comprises an insertion (with respect to 76G1) of from 5 to about 15 amino acids, such as from about 6 to about 12 amino acids, or about 6 or about 11 amino acids, after the position corresponding to positions 155 of SEQ ID NO: 5. In some embodiments, the insertion is a flexible and hydrophilic sequence, such as an amino acid sequence that is predominately Glycine and Serine residues. In some embodiments, the sequence is GSGGSG (SEQ ID NO: 7) or GSGGSGGSG (SEQ ID NO: 8).

In still other aspects and embodiments, the 1-3 UGT enzyme is not a circular permutant of UGT76G1, that is, the enzyme comprises an amino acid sequence that has at least about 75% sequence identity to the amino acid sequence of SEQ ID NO:1. In such embodiments, the enzyme may include one or more amino acid modifications described herein. Exemplary modifications of UGT76G1 (SEQ ID NO:1) include modifications with respect to SEQ ID NO:1 selected from: (i) a deletion of one or more amino acids corresponding to E74 to T81, (ii) a substitution at the position corresponding to position 357, which is optionally glycine, (iii) a substitution at the position corresponding to position 414, and which is optionally leucine, (iv) a substitution at the position corresponding to position 29, and which is optionally methionine, (v) a substitution at the position corresponding to position 402, which is optionally glutamine, (vi) a substitution at the position corresponding to position 154, which is optionally cysteine, (vii) a substitution at the position corresponding to position 194, and which is optionally phenylalanine, (viii) a substitution at the position corresponding to position 277, and which is optionally isoleucine, (ix) a substitution at the position corresponding to position 208, and which is optionally glutamine, (x) a substitution at the position corresponding to position 140, and which is optionally proline, and (xi) a substitution at the position corresponding to position 259, and which is optionally glutamic acid.

For example, in some embodiments, the UGT enzyme comprises a deletion of at least two, or at least three, at least four, at least five, at least six, at least seven, or all eight amino acids corresponding to E74 to T81 of SEQ ID NO:1. In various embodiments, the enzyme further comprises a substitution of alanine at the position corresponding to position 200 of SEQ ID NO: 1. In some embodiments, the enzyme has at least two, three, or four of: 357G, 414L, 29M, 402Q, 154C, 194F, 277I, 208Q, 140P, and 259E, each numbered according to SEQ ID NO:1.

In such embodiments, the enzyme may have is at least about 80% sequence identity, or at least about 85% sequence identity, or at least about 90% sequence identity, or at least about 95% sequence identity, or at least about 98% sequence identity to the amino acid sequence of SEQ ID NO:1. For example, the enzyme may have from 1 to 20, or from 1 to 10 amino acid modifications independently selected from amino acid substitutions, deletions, and insertions with respect to SEQ ID NO:1.

In still other aspects and embodiments, the 1-3 UGT enzyme is a circular permutant of SrUGT76G1 (see US 2017/0332673, which is hereby incorporated by reference in its entirety) and optionally having from 1 to 20 or from 1 to 15, or from 1 to 10 amino acid modifications independently selected from amino acid substitutions, deletions, and insertions with respect to the corresponding position of SEQ ID NO:1. Exemplary modifications with respect to positions of SEQ ID NO:1 can be selected from: (i) a deletion of one or more amino acids corresponding to E74 to T81 (as described herein), (ii) a substitution at the position corresponding to position 357, which is optionally glycine, (iii) a substitution at the position corresponding to position 414, and which is optionally leucine, (iv) a substitution at the position corresponding to position 29, and which is optionally methionine, (v) a substitution at the position corresponding to position 402, which is optionally glutamine, (vi) a substitution at the position corresponding to position 154, which is optionally cysteine, (vii) a substitution at the position corresponding to position 194, and which is optionally phenylalanine, (viii) a substitution at the position corresponding to position 277, and which is optionally isoleucine, (ix) a substitution at the position corresponding to position 208, and which is optionally glutamine, (x) a substitution at the position corresponding to position 140, and which is optionally proline, and (xi) a substitution at the position corresponding to position 259, and which is optionally glutamic acid. In some embodiments, the UGT enzyme comprises a deletion of the amino acids corresponding to E74 to T81.

Changes to the amino acid sequence of an enzyme can alter its activity or have no measurable effect. Silent changes with no measurable effect are most likely to be conservative substitutions and small insertions or deletions on solvent-exposed surfaces that are located away from active sites and substrate-binding sites. In contrast, enzymatic activity is more likely to be affected by non-conservative substitutions, large insertions or deletions, and changes within active sites, substrate-binding sites, and at buried positions important for protein folding or conformation. Changes that alter enzymatic activity may increase or decrease the reaction rate or increase or decrease the affinity or specificity for a particular substrate. For example, changes that increase the size of a substrate-binding site may permit an enzyme to act on larger substrates and changes that position a catalytic amino acid side chain closer to a target site on a substrate may increase the enzymatic rate.

Knowledge of the three-dimensional structure of an enzyme and the location of relevant active sites, substrate-binding sites, and other interaction sites can facilitate the rational design of mutations and provide mechanistic insight into the phenotype of specific changes. Plant UGTs share a highly conserved secondary and tertiary structure while having relatively low amino acid sequence identity. Osmani et al, Substrate specificity of plant UDP-dependent glycosyltransferases predicted from crystal structures and homology modeling, *Phytochemistry* 70 (2009) 325-347. The sugar acceptor and sugar donor substrates of UGTs are accommodated in a cleft formed between the N- and C-terminal domains. Several regions of the primary sequence contribute to the formation of the substrate binding pocket including structurally conserved domains as well as loop regions differing both with respect to their amino acid sequence and sequence length.

Construction of UGT derivatives can be guided based on structure analysis and homology modeling. See, Soon Goo Lee, et al., Molecular Basis for Branched Steviol Glucoside Biosynthesis, *PNAS*, Jun. 19, 2019.

For example, based on independent crystal structure preparation and analysis of SrUGT76G1_L200A and an amino acid sequence alignment of SrUGT76G1 to MbUGT3-1_1, it is predicted that the steviol core of stevioside is close (within 4 Å) to the following residues of MbUGT3-1_1: I244, L280, W351, A354, I357, M362, and T438. Further, the C19 1-2 glycosylation is predicted to be close (within 4 Å) to T438. The steviol core of RebD is predicted to be close (within 4 Å) of the following hydrophobic side chains of MbUGT3-1_1: L239, M242, I244, L280, I353, A354, and I357. The C13 1-2' glycosylation is predicted to be close (within 4 Å) of the following hydrogen bonding side chains of MbUGT3-1_1: S301 and D77. Positioning and amino acid content of the V341-Q352 and K355-A367 helices of MbUGT3-1_1 may be important for catalysis as the mutation corresponding to L200A is in a loop between these helices. Positions L76 and/or D77 of MbUGT3-1_1 may interact with the C13 glycosylation of stevioside.

Substitutions of amino acids may be conservative substitutions or non-conservative substitutions. Conservative substitutions are defined where the old and new amino acids have similar characteristics such as size and charge. Naturally occurring residues are divided into groups based on common side chain properties:

(group 1) hydrophobic (aliphatic): methionine (Met), Alanine (Ala), Valine (Val), Leucine (Leu), Isoleucine (Ile);

(group 2) neutral hydrophilic: Cysteine (Cys), Serine (Ser), Threonine (Thr), Asparagine (Asn), Glutamine (Gln);

(group 3) acidic: Aspartic acid (Asp), Glutamic acid (Glu);

(group 4) basic: Histidine (His), Lysine (Lys), Arginine (Arg);

(group 5) residues that influence chain orientation: Glycine (Gly), Proline (Pro); and (group 6) aromatic: Tryptophan (Trp), Tyrosine (Tyr), Phenylalanine (Phe).

Non-conservative substitutions will entail exchanging a member of one of these classes for another an amino acid of another class.

The amino acid sequence of the UGT enzyme can optionally include an alanine inserted or substituted at position 2 to decrease turnover in the cell. In various embodiments, the 1-3 UGT enzyme comprises an alanine amino acid residue inserted or substituted at position 2 with respect to SEQ ID NO: 5, 6, or 9, to provide additional stability in vivo.

Identity of amino acid sequences, i.e. the percentage of sequence identity, can be determined via sequence alignments. Such alignments can be carried out with several known algorithms, such as that described by Karlin and Altschul (Karlin & Altschul (1993) *Proc. Natl. Acad. Sci. USA* 90: 5873-5877), with hmmalign (HMMER package) or with the CLUSTAL algorithm (Thompson, J. D., Higgins, D. G. & Gibson, T. J. (1994) *Nucleic Acids Res.* 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) *J. Mol. Biol.* 215: 403-410. BLAST protein alignments may be performed with the BLASTP program, score=50, word length=3. To obtain gapped alignments for comparative purposes, Gapped BLAST is utilized as described in Altschul et al (1997) *Nucleic Acids Res.* 25: 3389-3402. When utilizing BLAST and Gapped BLAST programs, the default parameters of the respective programs are used.

In other aspects, the invention provides polynucleotides encoding the 1-3 UGT enzyme disclosed herein, as well as host cells comprising the same. The host cell may be a microorganism, a fungal cell, an algal cell, or a plant cell. The plant may be a stevia plant or, more particularly, a *Stevia rebaudiana* plant. Stevia plants naturally express the enzymes required to synthesize steviol and steviol glycosides, but they produce only trace amounts of highly glycosylated steviol glycosides such as RebM. In contrast, the RebM content of a stevia or *Stevia rebaudiana* plant expressing a polynucleotide encoding the 1-3 UGT may be more than about 1%, or more than about 2%, or more than about 5%, or more than about 10% of the steviol glycoside content of the plant leaves. Furthermore, the RebA content of a stevia or *Stevia rebaudiana* plant expressing a polynucleotide encoding the 1-3 UGT may be more than about 5%, or more than about 10%, or more than about 15% of the steviol glycoside content of the plant leaves.

The microbial host cell in various embodiments may be prokaryotic or eukaryotic. In some embodiments, the microbial host cell is a bacteria selected from *Escherichia* spp., *Bacillus* spp., *Corynebacterium* spp., *Rhodobacter* spp., *Zymomonas* spp., *Vibrio* spp., and *Pseudomonas* spp. For example, in some embodiments, the bacterial host cell is a species selected from *Escherichia coli*, *Bacillus subtilis*, *Corynebacterium glutamicum*, *Rhodobacter capsulatus*, *Rhodobacter sphaeroides*, *Zymomonas mobilis*, *Vibrio natriegens*, or *Pseudomonas putida*. In some embodiments, the bacterial host cell is *E. coli*. Alternatively, the microbial cell may be a yeast cell, such as but not limited to a species of *Saccharomyces, Pichia,* or *Yarrowia,* including *Saccharomyces cerevisiae, Pichia pastoris,* and *Yarrowia lipolytica.*

The polynucleotides encoding the 1-3 UGT enzymes may be integrated into the chromosome of the microbial cell, or alternatively, are expressed extrachromosomally. For example, the 1-3 UGT enzyme may be expressed from a bacterial artificial chromosome (BAC) or plasmid.

Expression of UGT enzymes can be tuned for optimal activity, using, for example, gene modules (e.g., operons) or independent expression of the UGT enzymes. For example, expression of the genes or operons can be regulated through selection of promoters, such as inducible or constitutive promoters, with different strengths (e.g., strong, intermediate, or weak). Several non-limiting examples of promoters of different strengths include Trc, T5 and T7. Additionally, expression of genes or operons can be regulated through manipulation of the copy number of the gene or operon in the cell. In some embodiments, the cell expresses a single copy of each UGT enzyme. In some embodiments, expression of genes or operons can be regulated through manipulating the order of the genes within a module, where the genes transcribed first are generally expressed at a higher level. In some embodiments, expression of genes or operons is regulated through integration of one or more genes or operons into the chromosome.

Optimization of UGT expression can also be achieved through selection of appropriate promoters and ribosomal binding sites. In some embodiments, this may include the selection of high-copy number plasmids, or single-, low- or medium-copy number plasmids. The step of transcription termination can also be targeted for regulation of gene expression, through the introduction or elimination of structures such as stem-loops.

In some embodiments, the cell is a plant cell. For example, the polynucleotide can be heterologously expressed in a stevia plant under the control of a suitable promoter, such as a constitutive or inducible promoter.

In the various embodiments, the host cell may express one or more additional UGT enzymes selected from C-13 UGT enzyme, a C-19 UGT enzyme, and a 1-2 UGT enzyme. In some embodiments, the host cell expresses (in addition to the 1-3 UGT enzyme) a heterologous C-13 UGT enzyme, a heterologous C-19 UGT enzyme, and a heterologous 1-2 UGT enzyme, and is thus capable of glycosylating steviol and steviol glycoside substrates to produce RebM.

FIG. 2 illustrates the structures of steviol and various steviol glycosides, and identifies enzymatic activities in biosynthetic pathways leading from steviol to RebM. Likewise, Table 1 identifies substrates and products on biosynthetic pathways leading from steviol to RebM. For each substrate and product pair, Table 1 describes the type of glycosylation and identifies enzymes with the requisite activity. Four types glycosylation activity are required for production of RebM: primary glycosylation of the C13 and C19 carbons, and secondary glycosylation at the 2' or 3' positions of the primary glycan. The glycans are added one 6-carbon monosaccharide unit at a time. Thus, a primary glycan must be conjugated to the C13 or C19 of steviol or a steviol glycoside before a secondary glycan can be conjugated to that primary glycan. However, the order of glycosylation of steviol glycosides is not otherwise restricted. Table 2 identifies enzymes from various sources with the activities required on biosynthetic pathways leading from steviol to Reb M and provides references for their nucleotide and amino acid sequences. See U.S. Patent Application Publication 20170332673, which is hereby incorporated by reference in its entirety.

TABLE 1

Enzymes catalyzing reactions leading to Reb M.

| Substrate | Product | Glycos. | Enzyme 1 | Enzyme 2 | Enzyme 3 | Enzyme 4 |
|---|---|---|---|---|---|---|
| Steviol | Steviolmonoside | C13 | SrUGT85C2 | | | |
| Steviol | C19-Glu-Steviol | C19 | SrUGT74G1 | MbUGTc19 | | |
| Steviolmonoside | Steviolbioside | 1-2' | SrUGT91D1 | SrUGT91D2 | OsUGT1-2 | MbUGT1-2 |
| Steviolmonoside | Rubusoside | C19 | SrUGT74G1 | MbUGTc19 | | |
| C19-Glu-Steviol | Rubusoside | C13 | SrUGT85C2 | | | |
| Steviolbioside | Stevioside | C19 | SrUGT74G1 | MbUGTc19 | | |
| Steviolbioside | RebB | 1-3' | SrUGT76G1 | MbUGT1-3_1 | | |
| Stevioside | RebE | 1-2' | SrUGT91D1 | SrUGT61D2 | OsUGT1-2 | MbUGT1-2 |
| Stevioside | Reb A | 1-3' | SrUGT76G1 | MbUGT1-3_1 | | |
| RebB | Reb A | C19 | SrUGT74G1 | MbUGTc19 | | |
| RebE | Reb D | 1-3' | SrUGT76G1 | MbUGT1-3_1 | | |
| Reb A | Reb D | 1-2' | SrUGT91D1 | SrUGT91D2 | OsUGT1-2 | MbUGT1-2 |
| Reb D | Reb M | 1-3' | SrUGT76G1 | MbUGT1-3_1 | MbUGT1-3_2 | |

TABLE 2

Enzyme/gene sequences for biosynthesis of steviol glycosides

| Glycosylation type | Enzyme | Gene ID | Protein ID | Description |
|---|---|---|---|---|
| C13 | SrUGT85C2 | AY345978.1 | AAR06916.1 | |
| C19 | SrUGT74G1 | AY345982.1 | AAR06920.1 | |
| | MbUGTc19 | — | — | US 2017/0332673 |
| 1-2' | SrUGT91D1 | AY345980.1 | AAR06918.1 | |
| | SrUGT91D2 | ACE87855.1 | ACE87855.1 | |
| | SrUGT91D2e | — | — | US 2011/038967 |
| | OsUGT1-2 | NM_001057542.1 | NP_001051007.2 | WO 2013/022989 |
| | MbUGT1-2 | — | — | US 2017/0332673 |

TABLE 2-continued

Enzyme/gene sequences for biosynthesis of steviol glycosides

| Glycosylation type | Enzyme | Gene ID | Protein ID | Description |
|---|---|---|---|---|
| 1-3' | SrUGT76G1 | FB917645.1 | CAX02464.1 | |
| | MbUGT1-3_1 | | | This disclosure |
| | MbUGT1-3_2 | | | This disclosure |

In some embodiments, the host cell produces steviol by expression of endogenous and/or heterologous enzymes for biosynthesis of steviol. The host cell may be engineered to co-express the 1-3 UGT with other UGT enzymes active on terpenoids and terpenoid glycosides, such as a C-13 UGT enzyme, a C-19 UGT enzyme, and a 1-2 UGT enzyme (see Tables 1-2). The microbial cell may additionally be engineered to co-express enzymes for steviol biosynthesis, such as enzymes of the MEP or MVA pathways, copalyl synthase and kaurene synthase (which can be present as a bifunctional enzyme in some embodiments), P450 enzymes such as kaurene oxidase and kaurenoic acid hydroxylase and P450 reductase enzymes. Table 3. Pathways and enzymes for biosynthesis of steviol are disclosed in US 20170332673, which is hereby incorporated by reference in its entirety.

steviol and/or steviol glycosides. In some embodiments, the substrate comprises stevioside and/or RebD. In various embodiments, the monosaccharide is glucose, galactose, fructose, rhamnose, or xylose. In some embodiments, the monosaccharide is glucose. In some embodiments, the method takes place in vitro with recombinant 1-3 UGT, and includes exogenously added NDP-sugar (e.g., UDP-glucose or ADP-glucose) reagent. In other embodiments, the 1-3 UGT is expressed recombinantly in a cell, and the NDP-glucose is available endogenously. In these embodiments, substrate can be fed to the cells, and is available in the cell for the glycosyltransferase reactions.

Whole cell conversion (i.e., a "biotransformation reaction") requires that substrate (e.g., glycoside intermediates) and product are transported into and out of the cell, respec-

TABLE 3

Summary of enzyme/gene sequences enabling biosynthesis of steviol.

| No. | Enzyme | Species | Gene ID | Protein ID |
|---|---|---|---|---|
| 1 | TcGGPPS | Taxus canadensis | AF081514.1 | AAD16018.1 |
| 2 | AgGGPPS | Abies grandis | AF425235.2 | AAL17614.2 |
| 3 | AnGGPPS | Aspergillus nidulans | XM_654104.1 | XP_659196.1 |
| 4 | SmGGPPS | Streptomyces melanosporofaciens | AB448947.1 | BAI44337.1 |
| 5 | MbGGPPS | Marine bacterium 443 | n/a | AAR37858.1 |
| 6 | PhGGPPS | Paracoccus haeundaensis | n/a | AAY28422.1 |
| 7 | CtGGPPS | Chlorobium tepidum TLS | NC_002932.3 | NP_661160.1 |
| 8 | SsGGPPS | Synechococcus sp. JA-3-3Ab | n/a | ABC98596.1 |
| 9 | Ss2GGPPS | Synechocystis sp. PCC 6803 | n/a | BAA16690.1 |
| 10 | TmGGPPS | Thermotoga maritima HB8 | n/a | NP_227976.1 |
| 11 | CgGGPPS | Corynebacterium glutamicum | n/a | NP_601376.2 |
| 12 | TtGGPPS | Thermus thermophillus HB27 | n/a | YP_143279.1 |
| 13 | PcGGPPS | Pyrobaculum calidifontis JCM 11548 | n/a | WP_011848845.1 |
| 14 | SrCPPS | Stevia rebaudiana | AF034545.1 | AAB87091.1 |
| 15 | EtCPPS | Erwina tracheiphila | n/a | WP_020322919.1 |
| 16 | SfCPPS | Sinorhizobium fredii | n/a | WP_010875301.1 |
| 17 | SrKS | Stevia rebaudiana | AF097311.1 | AAD34295.1 |
| 18 | EtKS | Erwina tracheiphila | n/a | WP_020322918.1 |
| 19 | SfKS | Sinorhizobium fredii | n/a | WP_010875302.1 |
| 20 | GfCPPS/KS | Gibberella fujikuroi | AB013295.1 | Q9UVY5.1 |
| 21 | PpCPPS/KS | Physcomitrella patens | AB302933.1 | BAF61135.1 |
| 22 | PsCPPS/KS | Phaeosphaeria sp. L487 | AB003395.1 | O13284.1 |
| 23 | AtKO | Arabidopsis thaliana | NM_122491.2 | NP_197962.1 |
| 24 | SrKO | Stevia rebaudiana | AY364317.1 | AAQ63464.1 |
| 25 | PpKO | Physcomitrella patens | AB618673.1 | BAK19917.1 |
| 26 | AtCPR | Arabidopsis thaliana | X66016.1 | CAA46814.1 |
| 27 | SrCPR | Stevia rebaudiana | DQ269454.4 | ABB88839.2 |
| 28 | AtKAH | Arabidopsis thaliana | NM_122399.2 | NP_197872.1 |
| 29 | SrKAH1 | Stevia rebaudiana | DQ398871.3 | ABD60225.1 |
| 30 | SrKAH2 | Stevia rebaudiana | n/a | n/a |

In some aspects, the invention provides a method for transferring a monosaccharide group to a substrate. The method comprises contacting an NDP-sugar (e.g., UDP-monosaccharide) and the substrate with the 1-3 UGT enzyme described herein, or a host cell expressing the 1-3 UGT enzyme or a lysate thereof. Various substrates can be glycosylated according to this disclosure, including but not limited to terpenoids. In some embodiments, the substrate is a terpenoid substrate, and can be a diterpenoid, such as tively, and that the cell provides UDP-glucose cofactor regeneration. This is in contrast to processes that use enzymes from cell lysis or secretion outside the cell, which requires an exogenous NDP-glucose supply or NDP-glucose precursor or NDP-glucose regeneration mechanism or NDP-glucose regeneration enzyme system. In embodiments of the present invention, catalysis (glycosylation) is carried out within live microbial cells. UDP-glucose cofactor recycling takes place using the native cellular metabolism without requiring externally provided enzymes or the feeding of expensive substrates. In accordance with some embodiments, glycoside intermediates are transported into the cell, and product is transported out of the cell.

US 2017/0332673 describes *E. coli* strains that overexpress MEP pathway enzymes, along with a downstream steviol biosynthesis pathway, and UGT enzymes to drive production of RebM from glucose. However, these strains do not perform biocatalysis of fed steviol glycoside intermediates to RebM, which may be, in part, due to the inability of the host cell to import the steviol glycoside substrate. In some embodiments, genetic modifications to the microbial cell allow for glycosylated intermediates to be translocated into the cell, while advanced glycosylated products are secreted into the medium.

In some embodiments, the microbial cell has one or more genetic modifications that increase UDP-glucose availability. In some embodiments, without wishing to be bound by theory, these modifications may also stress the cell for glucose availability, leading to the increased expression of endogenous transporters to import steviol glycosides into the cell. Wild-type UDP-glucose levels in exponentially growing *E. coli* is about 2.5 mM (Bennett B D, et al., Absolute metabolite concentrations and implied enzyme active site occupancy in *Escherichia coli*. *Nat Chem Biol*. 2009; 5(8): 593-9). In some embodiments, genetic modifications to the host cell are engineered to increase UDP-glucose, e.g., to at least 5 mM, or at least 10 mM, in exponentially growing cells (e.g., that do not have recombinant expression of UGT enzymes).

In some embodiments, the microbial cell has a deletion, inactivation, or reduced activity or expression of a gene encoding an enzyme that consumes UDP-glucose. For example, the microbial cell may have a deletion, inactivation, or reduced activity of ushA (UDP-sugar hydrolase) and/or one or more of galE, galT, galK, and galM (which are responsible for UDP-galactose biosynthesis from UDP-glucose), or ortholog thereof in the microbial species. In some embodiments, galETKM genes are inactivated, deleted, or substantially reduced in expression.

In these or other embodiments, the microbial cell has a deletion, inactivation, or reduced activity or expression of a gene encoding an enzyme that consumes a precursor to UDP-glucose. For example, in some embodiments, the microbial cell has a deletion, inactivation, or reduced activity or expression of pgi (glucose-6 phosphate isomerase), or ortholog thereof in the microbial species of the host cell.

In these or other embodiments, the cell has an overexpression or increased activity of one or more genes encoding an enzyme involved in converting glucose-6-phosphate to UDP-glucose. For example, pgm (phosphoglucomutase) and/or galU (UTP-glucose-1-phosphate uridylyltransferase) (or ortholog or derivative thereof) can be overexpressed, or modified to increase enzyme productivity. See, US 2020/0087692, which is hereby incorporated by reference in its entirety.

In some embodiments, the substrate is a plant extract, which is optionally a stevia leaf extract. In various embodiments, a microbial cell expressing the 1-3 UGT may be fed with steviol or a lower order steviol glycoside for the production of higher order steviol glycosides, including Reb D and Reb M. Advanced intermediates from stevia leaf extract are readily available from existing industrial extraction of steviol glycosides. As shown in Table 4, available leaf extract contains primarily the pathway intermediates stevioside and Rebaudioside A (RebA). In various embodiments, the stevia leaf extract is an extraction of steviol glycosides. In some embodiments, the extract comprises one or more of stevioside, steviolbioside, and Rebaudioside A, as prominent components. A prominent component generally makes up at least about 10% of the steviol glycosides in the extract, but in some embodiments, may make up at least about 20%, or at least about 25%, or at least about 30% of the steviol glycosides in the extract.

TABLE 4

Steviol Glycoside Composition of Available Stevia Leaf Extract

| % | Batch 1 | Batch 2 | Batch 3 |
| --- | --- | --- | --- |
| Rebaudioside A | 38.2 | 10.5 | 30.3 |
| Stevioside | 8.5 | 9.0 | 18.4 |
| Rebaudioside C | 12.9 | 4.2 | 16.6 |
| Rebaudioside B | 4.3 | 7.1 | 1.2 |
| Rubusoside | 5.0 | 2.2 | 2.0 |
| Rebaudioside F | 2.0 | 2.7 | 2.1 |
| Steviolbioside | 0.3 | 3.7 | 0.3 |
| Rebaudioside D | 0.2 | 2.1 | 0.9 |
| Dulcoside A | 0.9 | 0.4 | 0.5 |

In various embodiments, the 1-3 UGT converts a lower order steviol glycoside to a higher order steviol glycoside. For example, the UGT enzyme may have 1-3' UGT activity for the conversion of steviobioside to RebB, rubusoside to RebG, stevioside to Reb A, Reb A to RebI, RebG to Reb4, RebE to Reb D, and/or Reb D to Reb M. Alternatively, the UGT may be used in combination with another 1-3 UGT enzyme or enzymes having a preference of specificity for certain substrates. For example, one UGT may preferentially act as a 1-3 UGT on C13 glycosyl substrates whereas another UGT enzyme preferentially acts as a 1-3 UGT on C19 glycosyl substrates.

In some embodiments, a microbial cell expressing the 1-3 UGT enzyme is fed with RebD, and converts at least about 15%, or at least about 20%, or at least about 25%, or at least about 30%, or at least about 50%, or at least about 75%, or at least about 90% of the Reb D to Reb M. In various embodiments, such conversions are allowed to take place for at least about 8 hours, or at least about 24 hours in some embodiments. For example, the conversion may be allowed to take place in the culture for from 8 hours to about 72 hours. In some embodiments, the conversion may be allowed to take place for about 24 hours to about 60 hours. In some embodiments, the microbial cell converts at least about 40%, or at least about 50%, or at least about 75%, or at least about 90% of the Reb D to Reb M in about 48 hours or less or about 24 hours or less.

In some embodiments, the microbial cell is fed with stevioside and expresses the 1-3 UGT, and converts at least about 15%, or at least about 20%, or at least about 25%, or at least about 30%, or at least about 50% of the stevioside to Reb A. In some embodiments, the enzyme converts at least about 75% or at least about 90% of the stevioside to RebA. In various embodiments, such conversions are allowed to take place for at least about 8 hours, or at least about 24 hours in some embodiments. For example, the conversion may be allowed to take place in the culture for from 8 hours to about 72 hours. In some embodiments, the conversion may be allowed to take place for about 24 hours to about 60 hours. In some embodiments, the microbial cell converts at least about 40%, or at least about 50%, or at least about 75%, of the stevioside to RebA in about 48 hours or less or about 24 hours or less.

While the native UGT enzymes are generally plant enzymes (which often have optimal temperatures in the range of 20-24° C.) or are derived from plant enzymes, the present disclosure in some embodiments enables production of the glycosylated product at high yield in microbial cells (e.g., bacterial cells such as E. coli), with enzyme productivity at temperatures above 24° C., such as from 24° C. to 37° C., or from 27° C. to 37° C., or from 30° C. to 37° C. In some embodiments, culturing is conducted at from 30 to 34° C.

In some embodiments, the process is scalable for large-scale production. For example, in some embodiments, the size of the culture is at least about 100 L, at least about 200 L, at least about 500 L, at least about 1,000 L, or at least about 10,000 L, or at least about 100,000 L, or at least about 500,000 L.

In various embodiments, methods further include recovering glycosylated product from the cell culture or from cell lysates. In some embodiments, the culture produces at least about 100 mg/L, or at least about 200 mg/L, or at least about 500 mg/L, or at least about 1 g/L, or at least about 2 g/L, or at least about 5 g/L, or at least about 10 g/L, or at least about 20 g/L, or at least about 30 g/L, or at least about 40 g/L, or at least about 50 g/L of the glycosylated product, which in some embodiments is extracted from the culture media.

In some embodiments, the substrate is a terpenoid, such as a monoterpenoid, sesquiterpenoid, or triterpenoid. In some embodiments, the terpenoid is a triterpenoid, which is optionally mogrol or a mogroside. In some embodiments, the 1-3 UGT enzyme of the present disclosure has broad substrate activity towards glycosides, aliphatic and branched alcohols, substituted phenols, flavonoids and gallates. See e.g. Dewitt, G. et al., Screening of recombinant glycosyltransferases reveals the broad acceptor specificity of stevia UGT-76G1, *J. Biotechnology* 233 (2016) 49-55. Substrates of the UGT enzyme may include terpenoid glycosides (isoprenoids), including diterpenoid glycosides such as steviol glycosides and triterpenoid glycosides such as mogrosides.

In some embodiments, the method comprises growing the host cell in the presence of the substrate. The substrate may be fed to the culture, or in some embodiments, the substrate is synthesized by the host cell. In some embodiments, the substrate is steviol, and the host cell expresses a plurality of UGT enzymes to produce target steviol glycosides, such as RebM.

In some embodiments, the glycosylated products (e.g., RebM) are purified from media components. Thus, in some embodiments, the methods comprise separating growth media from *E. coli* cells, and isolating the desired glycosylation products (e.g, RebM) from the growth media. In some embodiments, product such as RebM is further extracted from the cellular material.

In some aspects, the invention provides methods for making a product comprising a glycosylated product, such as RebM. The method comprises incorporating the target steviol glycoside (produced according to this disclosure) into a product, such as a food, beverage, oral care product, sweetener, flavoring agent, or other product. Purified steviol glycosides, prepared in accordance with the present invention, may be used in a variety of products including, but not limited to, foods, beverages, texturants (e.g., starches, fibers, gums, fats and fat mimetics, and emulsifiers), pharmaceutical compositions, tobacco products, nutraceutical compositions, oral hygiene compositions, and cosmetic compositions. Non-limiting examples of flavors for which RebM can be used in combination include lime, lemon, orange, fruit, banana, grape, pear, pineapple, mango, bitter almond, cola, cinnamon, sugar, cotton candy and vanilla flavors. Non-limiting examples of other food ingredients include flavors, acidulants, and amino acids, coloring agents, bulking agents, modified starches, gums, texturizers, preservatives, antioxidants, emulsifiers, stabilizers, thickeners and gelling agents.

In some aspects, the invention provides methods for making a sweetener product comprising a plurality of high-intensity sweeteners, said plurality including two or more of a steviol glycoside, a mogroside, sucralose, aspartame, neotame, advantame, acesulfame potassium, saccharin, cyclamate, neohesperidin dihydrochalcone, gnetifolin E, and/or piceatannol 4'-O-β-D-glucopyranoside. The method may further comprise incorporating the sweetener product into a food, beverage, oral care product, sweetener, flavoring agent, or other product, including those described above.

Target steviol glycoside(s), such as RebM, and sweetener compositions comprising the same, can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory.

Further, target steviol glycoside(s), such as RebM, and sweetener compositions obtained according to this invention, may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, RebM and sweetener compositions can be used as a sweetener not only for drinks, foodstuffs, and other products dedicated for human consumption, but also in animal feed and fodder with improved characteristics.

Examples of products in which target steviol glycoside(s) and sweetener compositions may be used include, but are not limited to, alcoholic beverages such as vodka, wine, beer, liquor, and sake, natural juices, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Aspects and embodiments of the invention are now described with reference to the following examples.

EXAMPLES

Aspects and embodiments of the invention are now described with reference to the following examples.

Example 1: Screening of Mutants for MbUGT1-3_1 (SEQ ID NO: 5)

Plasmids comprising polynucleotides encoding UGT MbUGT1-3_1 (SEQ ID NO: 5) and 95 selected mutants were transformed into *E. coli* cells (ΔushA, ΔgalETKM, Δpgi; overexpressed pgm, galU). The resulting strains were seeded into a rich seed media and incubated overnight in 96-well plates at 250 rpm at 37° C. to make the seed cultures.

Production cultures were seeded with the seed cultures by adding 40 μL of the seed to 360 μL of fresh production media containing 0.5 mM Stevioside and 0.5 mM Rebaudioside D. The production culture was subsequently grown for 48 hours in 96-well plates at 250 rpm at 37° C. Products were quantified using a LC-MS QQQ.

The 95 mutants screened include the following (amino acid position of these mutants is with respect to MbUGT1-3_1 (SEQ ID NO: 5):

i) Substitution:

F11L, K13R, T16E, V18L, E19A, G48T, S62A, D73P, L89W, V93L, Y94E, W99F, E100C, N106R, E115K, Y119T, Q122E, K130W, V133A, V133S, M136K, S153L, G164R, R165N, R166G, I169L, F200L, F204H, F204P, K206A, K208D, K208N, F219D, F219S, L221P, R229A, I230F, L233I, G241A, R243M, P245S, I246L, R257D, E260A, L261K, L262Q, L264S, D269E, E271P, S273A, R294P, L296I, S301N, F304S, H309F, V310A, T327S, A333V, F336L, V341I, Y348T, Q352A, Q352D, Q352E, A354S, A354T, K355Y, L358I, M361Q, I362V, S375T, E383F, V387L, I388E, I388S, R389Q, L400F, L404F, A406S, D413E, V418C, P426A, S428K, S428G, V441I, D445E, D455N, Q457G, Q457K/S458Q, or Q457K.

ii) Substitution and Deletion:

Q457K and delete 5458 (ΔS458).

iii) Deletion:

ΔG159; ΔG159ΔG161; or ΔG159ΔS160ΔG161.

iv) Insertion:

Insertion of S between position 158 and 159 or insertion of K between 456 and 457.

All of the 95 mutants of MbUGT1-3_1 were screened for their ability to produce RebA and RebI as well as RebM from Stevioside (substrate). Table 5 shows the fold improvement of selected mutants of MbUGT1-3_1 to produce RebA and RebI (through 1-3 glucosylation at C-13-glucose) as well as RebM (through 1-3 glucosylation at C-19-glucose). In Table 5, column 2 generally corresponds to glycosylation at the C13-glucose of the substrate, while column 3 generally corresponds to glycosylation at the C19-glucose of the substrate. As shown, C-19 glycosylation is enhanced more than C-13 glycosylation. The mutant constructed with the mutations in Table 5 is referred to herein as MbUGT1-3_2 (SEQ ID NO: 6).

TABLE 5

| | MbUGT1-3_1 (lead mutations) | |
|---|---|---|
| Mutation | (RebA + RebI)/ (RebA + RebI + Stevioside) | RebM/(RebD + RebM + RebE) |
| Deletion G159_S160_G161 (ΔG159ΔS160ΔG161) | 1.13 | 1.25 |
| L262Q | 1.12 | 1.19 |
| R294P | 1.22 | 1.21 |
| D413E | 1.15 | 1.17 |

Example 2: Bioconversion by 1-3' Glycosylating Enzymes

Plasmids comprising polynucleotides encoding three UGTs, SrUGT76G1-L200A (SEQ ID NO: 1), MbUGT1-3_0 (SEQ ID NO: 4), MbUGT1-3_1 (SEQ ID NO: 5), and MbUGT1-3_2 (SEQ ID NO: 6) were individually transformed into *E. coli* cells (ΔushA, ΔgalETKM, Δpgi; overexpressed pgm, galU). The resulting strains were seeded into culture media containing 1 mM stevioside or 1 mM RebD. After growth, steviol glycosides were recovered from the culture media. Strains were grown overnight in 96-well plates at 250 rpm at 37° C. The cells were then transferred to a fresh production culture to 10% of the total volume. Each of stevioside (0.5 mM) and Rebaudioside D (0.5 mM) were included in the production culture. The production culture was then grown for 48 hours in 96-well plates at 250 rpm at 37° C. Products were quantified using a LC-MS QQQ.

Figure 4:
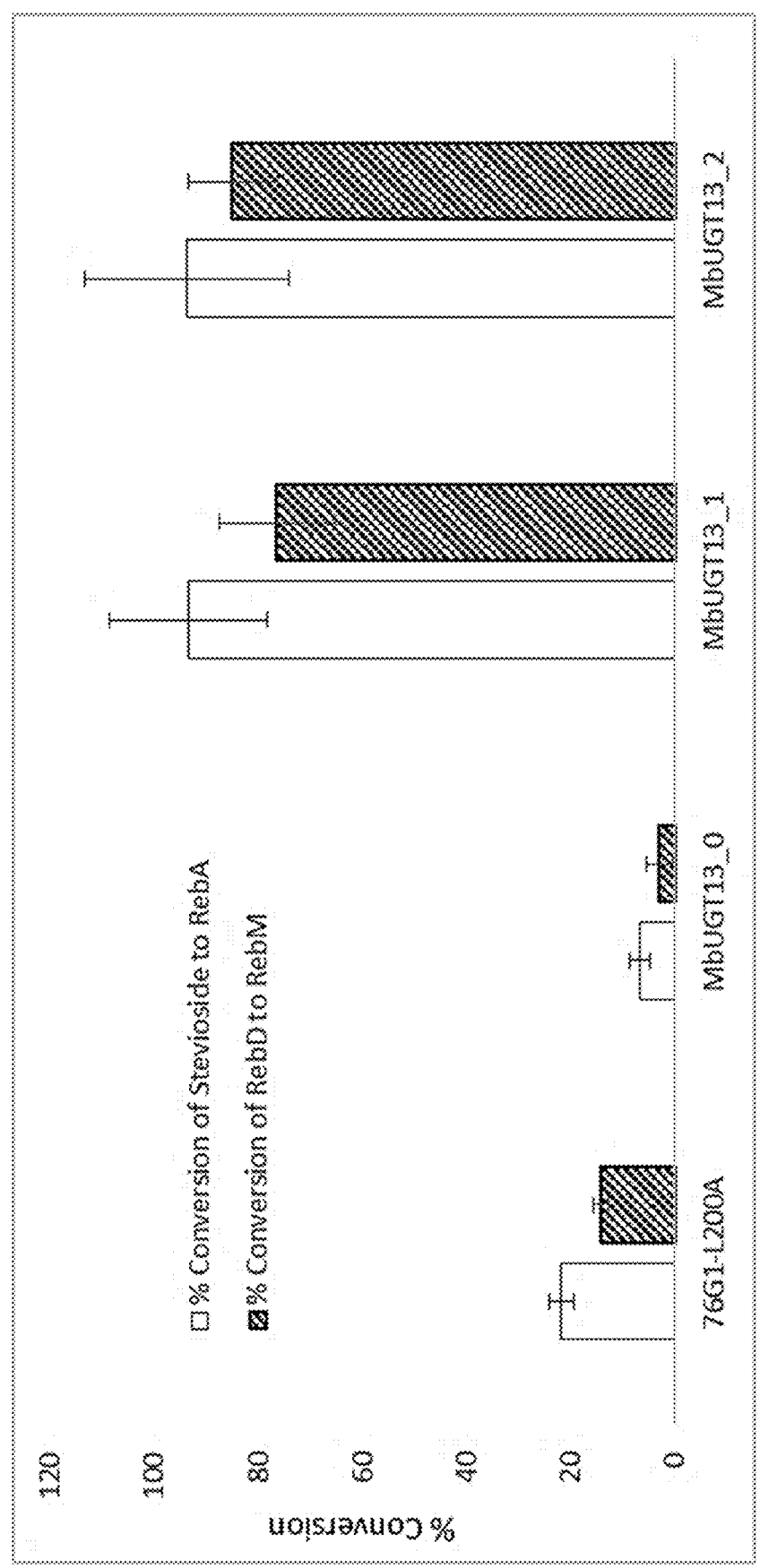
FIG. 4 shows the percent conversion of stevioside to RebA, and percent conversion of RebD to RebM in vitro by the following glycosyltransferases: UGT76G1-L200A (SEQ ID NO: 3), MbUGT1-3_0 (SEQ ID NO: 4), MbUGT1-3_1 (SEQ ID NO: 5), and MbUGT1-3_2 (SEQ ID NO: 6).
Figure 5:
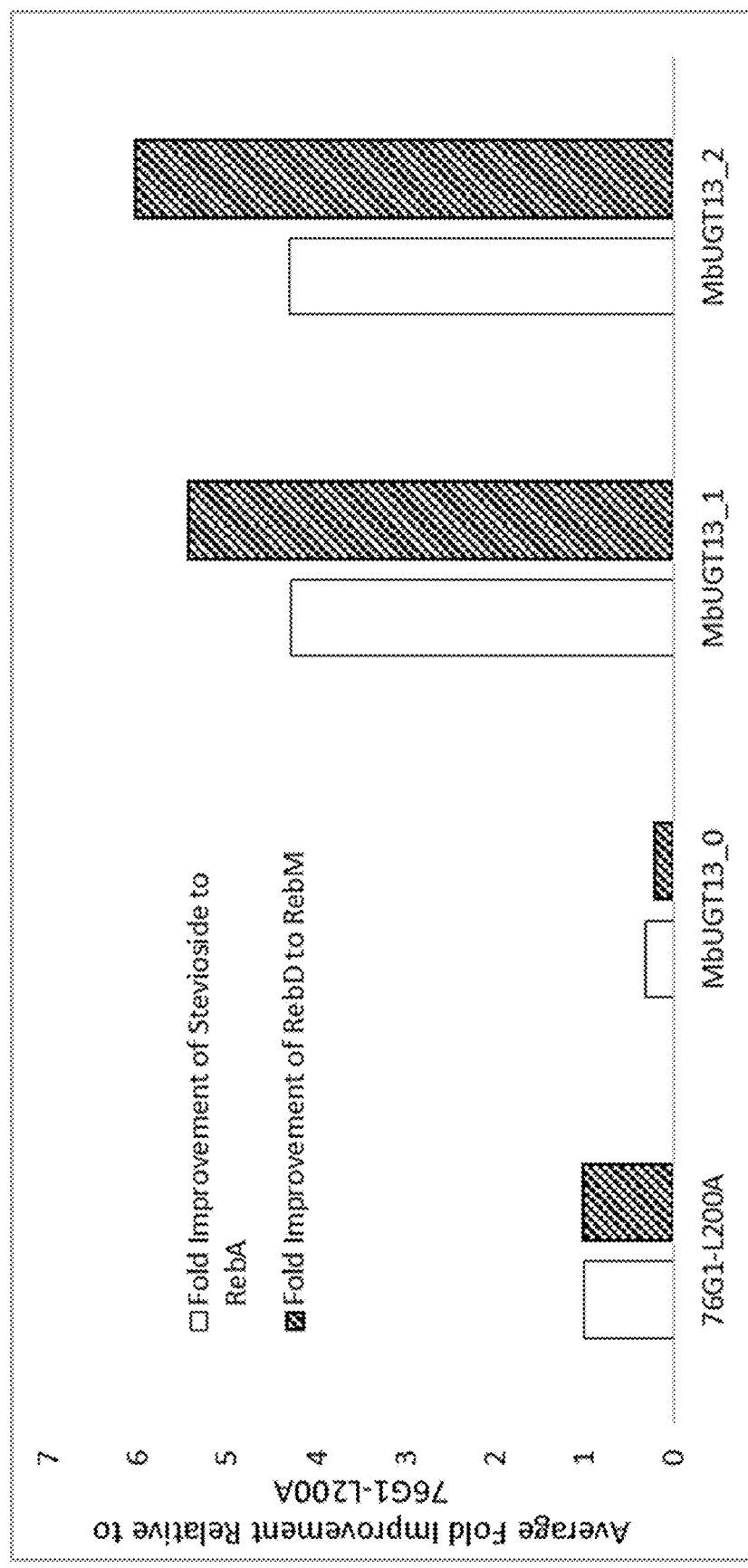
FIG. 5 shows the fold improvement for conversion of stevioside to RebA and for conversion of RebD to RebM, compared to UGT76G1-L200A. MbUGT1-3_1 and MbUGT1-3_2 show very stark improvements in enzyme productivity for both conversions.

FIG. 4 shows the percent conversion of stevioside to RebA and the percent conversion of RebD to RebM. The percent conversion for both reactions was highest for MbUGT1-3_1 and MbUGT1-3_2, which have the amino acid sequences of SEQ ID NO: 5 and SEQ ID NO: 6, respectively. FIG. 5 shows the fold improvement of MbUGT1-3_1 and MbUGT1-3_2 compared to SrUGT76G1-L200A.

Example 3: Screening of Mutants for MbUGT1-3_2 (SEQ ID NO: 6)

Plasmids comprising polynucleotides encoding UGT MbUGT1-3_2 (SEQ ID NO: 6) and 96 selected mutants of MbUGT1-3_2 were transformed into *E. coli* cells (ΔushA, ΔgalETKM, Δpgi; ΔaraA, overexpressed pgm, galU, UGT1-2 enzyme). The resulting strains were seeded into a rich seed media and incubated overnight in 96-well plates at 250 rpm at 37° C. to make the seed cultures.

Production cultures were then seeded with the seed cultures by adding 40 μL of the seed to 360 μL of fresh production media containing 1 g/L stevioside/RebA leaf extract. The production culture was then grown for 48 hours in 96-well plates at 250 rpm at 37° C. Products were quantified using a UPLC-DAD.

The mutants screened include the following (amino acid position is with respect to MbUGT1-3_1 (SEQ ID NO: 5):

i) Substitution:

T16G, V18L, E19A, D23E, R31K, C64S, I70V, L76N, P79M, W99F, D114E, R125L, V133A, S150D, T202M, F204E, Y212F, Y212H, R218L, D227S, E228S, I230F, I230Y, L233I, G237S/P238A, P238S, L239E, L239G, A240S, A240V, M242A, M242I, I246Y, I247F, A252I, D253E, L261K, L264E, A265D, E271P, S273A, C274G, C274L, Y282W, N292K,

S302G, L303M, F306W, L312M, Q314L, L318W, P323L, E331A, K340R, S346V, Y348F/S349D/ N350T/W351L/Q352E/I353N, Y348G/S349E/N350F/ W351G/Q352E/I353K, Y348T/S349N/N350E/ W351P/Q352E/I353E, W351F/Q352E/A354G, W351P, Q352D/A354G, Q352E, A354S, I362L, A367N, E383S, E385A, H403Y, L404F, F419K, S428K, L431I, D445E, D445I, A450L, or Q457G.

ii) Substitution and Deletion:
D227T and Δ228 to 234 iii) Deletion:
ΔG158 to G161; ΔG159 to G161; ΔS160 to ΔG161; ΔG161; Δ228; Δ228 to 229; Δ228 to 230; Δ228-231; Δ228 to 232; Δ228 to 233; Δ228 to 234; Δ228 to 235; Δ228 to 236; Δ228 to 237; ΔY320 to P323; ΔD325 to K326; or ΔK326.

iv) Insertion:
Insert LEA between F25 and L26;

iv) Replace:
Swap Y348-I353 with INPQG

Table 6 shows the ability of selected mutants of MbUGT1-3_2 (SEQ ID NO: 6) to produce RebM. Column 2 of Table 6 shows the fold improvement in the percentage of RebM in the reaction product.

TABLE 6

MbUGT1-3_2 lead mutations

| Mutation | Fold Improvement % RebM |
|---|---|
| Delete E225-T232 (ΔE225 to T232) | 11.1 |
| S72Q | 1.25 |
| A305C | 3.51 |
| Y345F | 3.97 |
| L428I | 2.48 |

The deletion of amino acids E225 to T232 produced a surprising 11 fold improvement in the production of RebM. Based on homology modeling, amino acids E225 to T232 appear to form a loop near the bound substrate. Deletion of amino acids E225-T232 may cause a shift in the substrate specificity of the UGT enzyme in favor of the RebD to RebM reaction. The sequence having a deletion of E225-T232 loop and S72Q, A305C, Y345F and L428I mutations with respect to MbUGT1-3_2 (SEQ ID NO: 6) is referred to as MbUGT1-3_3 (SEQ ID NO: 9).

Several deletions in the E225 to T232 region were tested, and these also showed enhancements in RebM production. Table 7 shows various beneficial deletions of the E225-T232 region (numbered according to SEQ ID NO:6)

TABLE 7

MbUGT1-3_2 Deletions

| Mutation | Fold Improvement % RebM |
|---|---|
| Delete E225-T232 | 11.1 |
| Delete E225-L230 | 3.2 |
| Delete E225-H233 | 3.2 |
| Delete E225-P231 | 3.1 |
| Delete E225-N229 | 1.7 |
| Delete E225-S228 | 1.6 |
| Delete E225 | 1.6 |
| Delete E225-I227 | 1.5 |
| Delete E225-G234 | 1.5 |

SEQUENCES

SEQ ID NO: 1
UGT76G1 [Stevia rebaudiana]
(SEQ ID NO: 1)
MENKTETTVRRRRRIILFPVPFQGHINPILQLANVLYSKGFSITIFHTNF
NKPKTSNYPHFTFRFILDNDPQDERISNLPTHGPLAGMRIPIINEHGADE
LRRELELLMLASEEDEEVSCLITDALWYFAQSVADSLNLRRLVLMTSSLF
NFHAHVSLPQFDELGYLDPDDKTRLEEQASGFPMLKVKDIKSAYSNWQIL
KEILGKMIKQTKASSGVIWNSFKELEESELETVIREIPAPSFLIPLPKHL
TASSSSLLDHDRTVFQWLDQQPPSSVLYVSFGSTSEVDEKDFLEIARGLV
DSKQSFLWVVRPGFVKGSTWVEPLPDGFLGERGRIVKWVPQQEVLAHGAI
GAFWTHSGWNSTLESVCEGVPMIFSDFGLDQPLNARYMSDVLKVGVYLEN
GWERGEIANAIRRVMVDEEGEYIRQNARVLKQKADVSLMKGGSSYESLES
LVSYISSL SEQ ID NO: 2
MbUGT1-3
Reference: US 2017/0332673
MANWQILKEILGKMIKQTKASSGVIWNSFKELEESELETVIREIPAPSFL
IPLPKHLTASSSSLLDHDRTVFQWLDQQPPSSVLYVSFGSTSEVDEKDFL
EIARGLVDSKQSFLWVVRPGFVKGSTWVEPLPDGFLGERGRIVKWVPQQE
VLAHGAIGAFWTHSGWNSTLESVCEGVPMIFSDFGLDQPLNARYMSDVLK
VGVYLENGWERGEIANAIRRVMVDEEGEYIRQNARVLKQKADVSLMKGGS
SYESLESLVSYISSLENKTETTVRRRRRIILFPVPFQGHINPILQLANVL
YSKGFSITIFHTNFNKPKTSNYPHFTFRFILDNDPQDERISNLPTHGPLA
GMRIPIINEHGADELRRELELLMLASEEDEEVSCLITDALWYFAQSVADS
LNLRRLVLMTSSLFNFHAHVSLPQFDELGYLDPDDKTRLEEQASGFPMLK
VKDIKSAYS SEQ ID NO: 3
UGT76G1 L200A
Reference: US 2017/0332673
MAENKTETTVRRRRRIILFPVPFQGHINPILQLANVLYSKGFSITIFHTN
FNKPKTSNYPHFTFRFILDNDPQDERISNLPTHGPLAGMRIPIINEHGAD
ELRRELELLMLASEEDEEVSCLITDALWYFAQSVADSLNLRRLVLMTSSL
FNFHAHVSLPQFDELGYLDPDDKTRLEEQASGFPMLKVKDIKSAYSNWQI
AKEILGKMIKQTKASSGVIWNSFKELEESELETVIREIPAPSFLIPLPKH
LTASSSSLLDHDRTVFQWLDQQPPSSVLYVSFGSTSEVDEKDFLEIARGL
VDSKQSFLWVVRPGFVKGSTWVEPLPDGFLGERGRIVKWVPQQEVLAHGA
IGAFWTHSGWNSTLESVCEGVPMIFSDFGLDQPLNARYMSDVLKVGVYLE
NGWERGEIANAIRRVMVDEEGEYIRQNARVLKQKADVSLMKGGSSYESLE
SLVSYISSL SEQ ID NO: 4
MbUGT1-3_0
MAKQSFLWVVRPGFVKGSTWVEPLPDGFLGERGRIVKWVPQQEVLAHGAI
GAFWTHSGWNSTLESVCEGVPMIFSDFGLDQPLNARYMSDVLKVGVYLEN
GWERGEIANAIRRVMVDEEGEYIRQNARVLKQKADVSLMKGGSSYESLES
LVSYISSLENKTETTVRRRRRIILFPVPFQGHINPILQLANVLYSKGFSI
TIFHTNFNKPKTSNYPHFTFRFILDNDPQDERISNLPTHGPLAGMRIPII
NEHGADELRRELELLMLASEEDEEVSCLITDALWYFAQSVADSLNLRRLV
LMTSSLFNFHAHVSLPQFDELGYLDPDDKTRLEEQASGFPMLKVKDIKSA
YSNWQIAKEILGKMIKQTKASSGVIWNSFKELEESELETVIREIPAPSFL
IPLPKHLTASSSSLLDHDRTVFQWLDQQPPSSVLYVSFGSTSEVDEKDFL
EIARGLVDS SEQ ID NO: 5
MbUGT1-3_1
MAFLWVVRPGFVKGSTWVEPLPDGFLGERGRIVKWVPQQEVLAHGAIGAF
WTHGGWNSTLESVCEGVPMIFSDEGLDQPLNARYMSDVLKVGVYLENGWE
RGEIANAIRRLMVDEEGEYIRQNARVLKQKADVSLMKGGSSYESLESLVS
YISSLGSGGSGGSGRRRRIILFPVPFQGHINPMLQLANVLYSKGFSITIF
HTNFNKPKTSNYPHFTFRFILDNDPQDERISNLPTHGPLAGMRIPIINEH
GADELRRELELLMLASEEDEEVSCLITDALWYFAQSVADSLNLRRLVLMT
SSLFNFHAHVSLPQFDELGYLDPDDKTRLEEQASGFPMLKVKDIKSAYSN
WQIAKEILGKMIKQTKASSGVIWNSFKELEESELETVIREIPAPSFLIPL
PKHLTASSSSLLDHDRTVFQWLDQQPPSSVLYVSFGSTSEVDEKDFLEIA
RGLVDSQS SEQ ID NO: 6
MbUGT1-3_2
MAFLWVVRPGFVKGSTWVEPLPDGFLGERGRIVKWVPQQEVLAHGAIGAF
WTHGGWNSTLESVCEGVPMIFSDEGLDQPLNARYMSDVLKVGVYLENGWE
RGEIANAIRRLMVDEEGEYIRQNARVLKQKADVSLMKGGSSYESLESLVS
YISSLGSGGSGRRRRIILFPVPFQGHINPMLQLANVLYSKGFSITIFHTN
FNKPKTSNYPHFTFRFILDNDPQDERISNLPTHGPLAGMRIPIINEHGAD
ELRRELELQMLASEEDEEVSCLITDALWYFAQSVADSLNLPRLVLMTSSL
FNFHAHVSLPQFDELGYLDPDDKTRLEEQASGFPMLKVKDIKSAYSNWQI

| SEQUENCES |
|---|
| AKEILGKMIKQTKASSGVIWNSFKELEESELETVIREIPAPSFLIPLPKH
LTASSSSLLEHDRTVFQWLDQQPPSSVLYVSFGSTSEVDEKDFLEIARGL
VDSQS |
| SEQ ID NO: 7
Linker
GSGGSG |
| SEQ ID NO: 8
Linker
GSGGSGGSG |
| SEQ ID NO: 9
MbUGT1-3_3
MAFLWVVRPGFVKGSTWVEPLPDGFLGERGRIVKWVPQQEVLAHGAIGAF
WTHGGWNSTLESVCEGVPMIFQDFGLDQPLNARYMSDVLKVGVYLENGWE
RGEIANAIRRLMVDEEGEYIRQNARVLKQKADVSLMKGGSSYESLESLVS
YISSLGSGGSGRRRRIILFPVPFQGHINPMLQLANVLYSKGFSITIFHTN
FNKPKTSNYPHFTFRFILDNDPQDHGPLAGMRIPIINEHGADELRRELEL
QMLASEEDEEVSCLITDALWYFAQSVADSLNLPRLVLMTSSLFNFHCHVS
LPQFDELGYLDPDDKTRLEEQASGPPMLKVKDIKSAFSNWQIAKEILGKM
IKQTKASSGVIWNSFKELEESELETVIREIPAPSFLIPLPKHLTASSSSL
LEHDRIVFQWLDQQPPSSVIYVSFGSTSEVDEKDFLEIARGLVDSQS |

The invention claimed is:

1. A uridine diphosphate-dependent glycosyltransferase (UGT) enzyme comprising an amino acid sequence that is at least 85% identical to the amino acid sequence of SEQ ID NO: 5 or SEQ ID NO: 6, wherein:
   the enzyme has an insertion with respect to SEQ ID NO: 1 of a flexible and hydrophilic sequence of 6 to 12 amino acids that is predominately Glycine and Serine residues after the position corresponding to position 155 of SEQ ID NO: 5; and
   the enzyme retains one or more of:
   a glycine (G) at the position corresponding to position 54 of SEQ ID NO: 5;
   a leucine (L) at the position corresponding to position 111 of SEQ ID NO: 5; and
   a methionine (M) at the position corresponding to position 183 of SEQ ID NO: 5.

2. The enzyme of claim 1, wherein the amino acid sequence is at least 95% identical to SEQ ID NO: 5 or SEQ ID NO: 6.

3. The enzyme of claim 1, wherein the enzyme has Gly at the position corresponding to position 54 of SEQ ID NO: 5, Leu at the position corresponding to position 111 of the SEQ ID NO: 5, and a Met at the position corresponding to position 183 of SEQ ID NO: 5.

4. The enzyme of claim 1, wherein the insertion is GSGGSG (SEQ ID NO: 7) or GSGGSGGSG (SEQ ID NO: 8).

5. The enzyme of claim 1, wherein the enzyme comprises a deletion of at least three amino acids corresponding to amino acids E225 to T232 with respect to the amino acid sequence of SEQ ID NO: 6.

6. The enzyme of claim 5, wherein the enzyme comprises a deletion of the amino acids corresponding to amino acids E225 to T232 of SEQ ID NO: 6.

7. The enzyme of claim 1, wherein the enzyme comprises an amino acid substitution at one or more positions corresponding to position 72, position 305, position 345, and position 428 of SEQ ID NO: 6.

8. The enzyme of claim 7, wherein the enzyme comprises one or more amino acid substitutions selected from: a glutamine (Q) at the position corresponding to position 72 of SEQ ID NO: 6; a cysteine (C) at the position corresponding to position 305 of SEQ ID NO: 6; a phenylalanine (F) at the position corresponding to position 345 of SEQ ID NO: 6; and an isoleucine (I) at the position corresponding to position 428 of SEQ ID NO: 6.

9. A uridine diphosphate-dependent glycosyltransferase (UGT) enzyme comprising an amino acid sequence that is at least 85% identical to the amino acid sequence of SEQ ID NO: 5 or SEQ ID NO: 6, wherein the UGT enzyme comprises:
   a glycine (G) at the position corresponding to position 54 of SEQ ID NO: 5;
   a leucine (L) at the position corresponding to position 111 of SEQ ID NO: 5; and
   a methionine (M) at the position corresponding to position 183 of SEQ ID NO: 5.

10. A uridine diphosphate-dependent glycosyltransferase (UGT) enzyme comprising an amino acid sequence that has at least 85% sequence identity to the amino acid sequence of SEQ ID NO:1, and comprising a deletion of amino acids corresponding to E74 to T81 of SEQ ID NO: 1.

11. A uridine diphosphate-dependent glycosyltransferase (UGT) enzyme that is a circular permutant of SrUGT76G1 (SEQ ID NO: 1), and having from 1 to 20 amino acid modifications independently selected from amino acid substitutions, deletions, and insertions with respect to the corresponding position of SEQ ID NO:1, with the proviso that the circular permutant has a deletion of amino acids corresponding to amino acids E74 to T81 of SEQ ID NO: 1.

12. The enzyme of claim 5, wherein the enzyme comprises a deletion of at least five amino acids corresponding to amino acids E74 to T81 with respect to the amino acid sequence of SEQ ID NO: 6.

13. The enzyme of claim 7, wherein the enzyme comprises a substitution of glutamine (Q) or asparagine (N) at the position corresponding to position 72 of SEQ ID NO: 6.

14. The enzyme of claim 7, wherein the enzyme comprises a neutral hydrophilic amino acid selected from cysteine (C), Serine (S), or Threonine (T) at the position corresponding to position 305 of SEQ ID NO: 6.

15. The enzyme of claim 7, wherein the enzyme comprises a substitution of phenylalanine (F) or Tryptophan (W) at the position corresponding to position 345 of SEQ ID NO: 6.

16. The enzyme of claim 7, wherein the enzyme comprises a substitution of isoleucine (I), valine (V), or alanine (A) at the position corresponding to position 428 of SEQ ID NO: 6.

17. The enzyme of claim 7, wherein the enzyme comprises 2, 3, or 4 of the following substitutions with respect to SEQ ID NO: 6: S72Q, A305C, Y345F, and L428I.

18. A uridine diphosphate-dependent glycosyltransferase (UGT) enzyme comprising an amino acid sequence that is at least 85% identical to the amino acid sequence of SEQ ID NO: 5 or SEQ ID NO: 6, and comprising a deletion of at least three amino acids corresponding to amino acids E225 to T232 with respect to SEQ ID NO: 6.

19. The UGT enzyme of claim 18, wherein the enzyme comprises a deletion of at least five amino acids corresponding to amino acids E225 to T232 with respect to SEQ ID NO: 6.

20. The UGT enzyme of claim 18, wherein the enzyme comprises a deletion of the amino acids corresponding to amino acids E225 to T232 with respect to SEQ ID NO: 6.

21. The UGT enzyme of claim 18, wherein the enzyme is at least 90% identical to SEQ ID NO: 5 or SEQ ID NO: 6.

22. The UGT enzyme of claim 18, wherein the enzyme is at least 95% identical to SEQ ID NO: 5 or SEQ ID NO: 6.

23. A polynucleotide encoding the enzyme of any one of claims 1, 9, 10, 11 or 18.

24. An isolated recombinant microorganism comprising the polynucleotide of claim 23.

25. A method for transferring a monosaccharide group to a substrate comprising contacting a NDP-sugar and the substrate with the isolated recombinant microorganism of claim 24.

26. A method for transferring a glycosyl group to a substrate comprising growing the isolated recombinant microorganism of claim 24 in the presence of the substrate.

* * * * *

SEQUENCE LISTING

<160> NUMBER OF SEQ ID NOS: 9

<210> SEQ ID NO 1
<211> LENGTH: 458
<212> TYPE: PRT
<213> ORGANISM: Stevia rebaudiana

<400> SEQUENCE: 1

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270
```

```
Pro Ser Ser Val Leu Tyr Val Ser Phe Gly Ser Thr Ser Glu Val Asp
    275                 280                 285

Glu Lys Asp Phe Leu Glu Ile Ala Arg Gly Leu Val Asp Ser Lys Gln
290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
                355                 360                 365

Gly Val Pro Met Ile Phe Ser Asp Phe Gly Leu Asp Gln Pro Leu Asn
                370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430

Lys Ala Asp Val Ser Leu Met Lys Gly Gly Ser Ser Tyr Glu Ser Leu
                435                 440                 445

Glu Ser Leu Val Ser Tyr Ile Ser Ser Leu
                450                 455

<210> SEQ ID NO 2
<211> LENGTH: 459
<212> TYPE: PRT
<213> ORGANISM: Stevia rebaudiana

<400> SEQUENCE: 2

Met Ala Asn Trp Gln Ile Leu Lys Glu Ile Leu Gly Lys Met Ile Lys
1               5                   10                  15

Gln Thr Lys Ala Ser Ser Gly Val Ile Trp Asn Ser Phe Lys Glu Leu
                20                  25                  30

Glu Glu Ser Glu Leu Glu Thr Val Ile Arg Glu Ile Pro Ala Pro Ser
                35                  40                  45

Phe Leu Ile Pro Leu Pro Lys His Leu Thr Ala Ser Ser Ser Ser Leu
            50                  55                  60

Leu Asp His Asp Arg Thr Val Phe Gln Trp Leu Asp Gln Gln Pro Pro
65                  70                  75                  80

Ser Ser Val Leu Tyr Val Ser Phe Gly Ser Thr Ser Glu Val Asp Glu
                85                  90                  95

Lys Asp Phe Leu Glu Ile Ala Arg Gly Leu Val Asp Ser Lys Gln Ser
                100                 105                 110

Phe Leu Trp Val Val Arg Pro Gly Phe Val Lys Gly Ser Thr Trp Val
            115                 120                 125

Glu Pro Leu Pro Asp Gly Phe Leu Gly Glu Arg Gly Arg Ile Val Lys
130                 135                 140

Trp Val Pro Gln Gln Glu Val Leu Ala His Gly Ala Ile Gly Ala Phe
145                 150                 155                 160

Trp Thr His Ser Gly Trp Asn Ser Thr Leu Glu Ser Val Cys Glu Gly
                165                 170                 175

Val Pro Met Ile Phe Ser Asp Phe Gly Leu Asp Gln Pro Leu Asn Ala
```

```
                    180                 185                 190
Arg Tyr Met Ser Asp Val Leu Lys Val Gly Val Tyr Leu Glu Asn Gly
            195                 200                 205

Trp Glu Arg Gly Glu Ile Ala Asn Ala Ile Arg Arg Val Met Val Asp
        210                 215                 220

Glu Glu Gly Glu Tyr Ile Arg Gln Asn Ala Arg Val Leu Lys Gln Lys
225                 230                 235                 240

Ala Asp Val Ser Leu Met Lys Gly Gly Ser Ser Tyr Glu Ser Leu Glu
                245                 250                 255

Ser Leu Val Ser Tyr Ile Ser Ser Leu Glu Asn Lys Thr Glu Thr Thr
            260                 265                 270

Val Arg Arg Arg Arg Ile Ile Leu Phe Pro Val Pro Phe Gln Gly
        275                 280                 285

His Ile Asn Pro Ile Leu Gln Leu Ala Asn Val Leu Tyr Ser Lys Gly
        290                 295                 300

Phe Ser Ile Thr Ile Phe His Thr Asn Phe Asn Lys Pro Lys Thr Ser
305                 310                 315                 320

Asn Tyr Pro His Phe Thr Phe Arg Phe Ile Leu Asp Asn Asp Pro Gln
                325                 330                 335

Asp Glu Arg Ile Ser Asn Leu Pro Thr His Gly Pro Leu Ala Gly Met
            340                 345                 350

Arg Ile Pro Ile Ile Asn Glu His Gly Ala Asp Glu Leu Arg Arg Glu
        355                 360                 365

Leu Glu Leu Leu Met Leu Ala Ser Glu Glu Asp Glu Glu Val Ser Cys
370                 375                 380

Leu Ile Thr Asp Ala Leu Trp Tyr Phe Ala Gln Ser Val Ala Asp Ser
385                 390                 395                 400

Leu Asn Leu Arg Arg Leu Val Leu Met Thr Ser Ser Leu Phe Asn Phe
                405                 410                 415

His Ala His Val Ser Leu Pro Gln Phe Asp Glu Leu Gly Tyr Leu Asp
            420                 425                 430

Pro Asp Asp Lys Thr Arg Leu Glu Glu Gln Ala Ser Gly Phe Pro Met
        435                 440                 445

Leu Lys Val Lys Asp Ile Lys Ser Ala Tyr Ser
        450                 455

<210> SEQ ID NO 3
<211> LENGTH: 459
<212> TYPE: PRT
<213> ORGANISM: Stevia rebaudiana

<400> SEQUENCE: 3

Met Ala Glu Asn Lys Thr Glu Thr Thr Val Arg Arg Arg Arg Ile
1               5                   10                  15

Ile Leu Phe Pro Val Pro Phe Gln Gly His Ile Asn Pro Ile Leu Gln
            20                  25                  30

Leu Ala Asn Val Leu Tyr Ser Lys Gly Phe Ser Ile Thr Ile Phe His
        35                  40                  45

Thr Asn Phe Asn Lys Pro Lys Thr Ser Asn Tyr Pro His Phe Thr Phe
    50                  55                  60

Arg Phe Ile Leu Asp Asn Asp Pro Gln Asp Glu Arg Ile Ser Asn Leu
65                  70                  75                  80

Pro Thr His Gly Pro Leu Ala Gly Met Arg Ile Pro Ile Ile Asn Glu
                85                  90                  95
```

```
His Gly Ala Asp Glu Leu Arg Arg Glu Leu Glu Leu Leu Met Leu Ala
            100                 105                 110

Ser Glu Glu Asp Glu Glu Val Ser Cys Leu Ile Thr Asp Ala Leu Trp
        115                 120                 125

Tyr Phe Ala Gln Ser Val Ala Asp Ser Leu Asn Leu Arg Arg Leu Val
    130                 135                 140

Leu Met Thr Ser Ser Leu Phe Asn Phe His Ala His Val Ser Leu Pro
145                 150                 155                 160

Gln Phe Asp Glu Leu Gly Tyr Leu Asp Pro Asp Lys Thr Arg Leu
                165                 170                 175

Glu Glu Gln Ala Ser Gly Phe Pro Met Leu Lys Val Lys Asp Ile Lys
            180                 185                 190

Ser Ala Tyr Ser Asn Trp Gln Ile Ala Lys Glu Ile Leu Gly Lys Met
        195                 200                 205

Ile Lys Gln Thr Lys Ala Ser Ser Gly Val Ile Trp Asn Ser Phe Lys
    210                 215                 220

Glu Leu Glu Glu Ser Glu Leu Glu Thr Val Ile Arg Glu Ile Pro Ala
225                 230                 235                 240

Pro Ser Phe Leu Ile Pro Leu Pro Lys His Leu Thr Ala Ser Ser Ser
                245                 250                 255

Ser Leu Leu Asp His Asp Arg Thr Val Phe Gln Trp Leu Asp Gln Gln
            260                 265                 270

Pro Pro Ser Ser Val Leu Tyr Val Ser Phe Gly Ser Thr Ser Glu Val
        275                 280                 285

Asp Glu Lys Asp Phe Leu Glu Ile Ala Arg Gly Leu Val Asp Ser Lys
    290                 295                 300

Gln Ser Phe Leu Trp Val Val Arg Pro Gly Phe Val Lys Gly Ser Thr
305                 310                 315                 320

Trp Val Glu Pro Leu Pro Asp Gly Phe Leu Gly Glu Arg Gly Arg Ile
                325                 330                 335

Val Lys Trp Val Pro Gln Gln Glu Val Leu Ala His Gly Ala Ile Gly
            340                 345                 350

Ala Phe Trp Thr His Ser Gly Trp Asn Ser Thr Leu Glu Ser Val Cys
        355                 360                 365

Glu Gly Val Pro Met Ile Phe Ser Asp Phe Gly Leu Asp Gln Pro Leu
    370                 375                 380

Asn Ala Arg Tyr Met Ser Asp Val Leu Lys Val Gly Val Tyr Leu Glu
385                 390                 395                 400

Asn Gly Trp Glu Arg Gly Glu Ile Ala Asn Ala Ile Arg Arg Val Met
                405                 410                 415

Val Asp Glu Glu Gly Glu Tyr Ile Arg Gln Asn Ala Arg Val Leu Lys
            420                 425                 430

Gln Lys Ala Asp Val Ser Leu Met Lys Gly Gly Ser Ser Tyr Glu Ser
        435                 440                 445

Leu Glu Ser Leu Val Ser Tyr Ile Ser Ser Leu
    450                 455

<210> SEQ ID NO 4
<211> LENGTH: 459
<212> TYPE: PRT
<213> ORGANISM: Stevia rebaudiana

<400> SEQUENCE: 4

Met Ala Lys Gln Ser Phe Leu Trp Val Val Arg Pro Gly Phe Val Lys
1               5                   10                  15
```

```
Gly Ser Thr Trp Val Glu Pro Leu Pro Asp Gly Phe Leu Gly Glu Arg
         20              25              30
Gly Arg Ile Val Lys Trp Val Pro Gln Gln Glu Val Leu Ala His Gly
         35              40              45
Ala Ile Gly Ala Phe Trp Thr His Ser Gly Trp Asn Ser Thr Leu Glu
 50              55              60
Ser Val Cys Glu Gly Val Pro Met Ile Phe Ser Asp Phe Gly Leu Asp
 65              70              75              80
Gln Pro Leu Asn Ala Arg Tyr Met Ser Asp Val Leu Lys Val Gly Val
                 85              90              95
Tyr Leu Glu Asn Gly Trp Glu Arg Gly Glu Ile Ala Asn Ala Ile Arg
                100             105             110
Arg Val Met Val Asp Glu Glu Gly Tyr Ile Arg Gln Asn Ala Arg
             115             120             125
Val Leu Lys Gln Lys Ala Asp Val Ser Leu Met Lys Gly Gly Ser Ser
         130             135             140
Tyr Glu Ser Leu Glu Ser Leu Val Ser Tyr Ile Ser Ser Leu Glu Asn
145             150             155             160
Lys Thr Glu Thr Thr Val Arg Arg Arg Arg Ile Ile Leu Phe Pro
                 165             170             175
Val Pro Phe Gln Gly His Ile Asn Pro Ile Leu Gln Leu Ala Asn Val
             180             185             190
Leu Tyr Ser Lys Gly Phe Ser Ile Thr Ile Phe His Thr Asn Phe Asn
             195             200             205
Lys Pro Lys Thr Ser Asn Tyr Pro His Phe Thr Phe Arg Phe Ile Leu
         210             215             220
Asp Asn Asp Pro Gln Asp Glu Arg Ile Ser Asn Leu Pro Thr His Gly
225             230             235             240
Pro Leu Ala Gly Met Arg Ile Pro Ile Ile Asn Glu His Gly Ala Asp
                 245             250             255
Glu Leu Arg Arg Glu Leu Glu Leu Met Leu Ala Ser Glu Glu Asp
             260             265             270
Glu Glu Val Ser Cys Leu Ile Thr Asp Ala Leu Trp Tyr Phe Ala Gln
             275             280             285
Ser Val Ala Asp Ser Leu Asn Leu Arg Arg Leu Val Leu Met Thr Ser
         290             295             300
Ser Leu Phe Asn Phe His Ala His Val Ser Leu Pro Gln Phe Asp Glu
305             310             315             320
Leu Gly Tyr Leu Asp Pro Asp Asp Lys Thr Arg Leu Glu Glu Gln Ala
                 325             330             335
Ser Gly Phe Pro Met Leu Lys Val Lys Asp Ile Lys Ser Ala Tyr Ser
             340             345             350
Asn Trp Gln Ile Ala Lys Glu Ile Leu Gly Lys Met Ile Lys Gln Thr
             355             360             365
Lys Ala Ser Ser Gly Val Ile Trp Asn Ser Phe Lys Glu Leu Glu Glu
         370             375             380
Ser Glu Leu Glu Thr Val Ile Arg Glu Ile Pro Ala Pro Ser Phe Leu
385             390             395             400
Ile Pro Leu Pro Lys His Leu Thr Ala Ser Ser Ser Leu Leu Asp
             405             410             415
His Asp Arg Thr Val Phe Gln Trp Leu Asp Gln Gln Pro Pro Ser Ser
             420             425             430
```

```
Val Leu Tyr Val Ser Phe Gly Ser Thr Ser Glu Val Asp Glu Lys Asp
            435                 440                 445

Phe Leu Glu Ile Ala Arg Gly Leu Val Asp Ser
    450                 455

<210> SEQ ID NO 5
<211> LENGTH: 458
<212> TYPE: PRT
<213> ORGANISM: Stevia rebaudiana

<400> SEQUENCE: 5

Met Ala Phe Leu Trp Val Val Arg Pro Gly Phe Val Lys Gly Ser Thr
1               5                   10                  15

Trp Val Glu Pro Leu Pro Asp Gly Phe Leu Gly Glu Arg Gly Arg Ile
            20                  25                  30

Val Lys Trp Val Pro Gln Gln Glu Val Leu Ala His Gly Ala Ile Gly
        35                  40                  45

Ala Phe Trp Thr His Gly Gly Trp Asn Ser Thr Leu Glu Ser Val Cys
    50                  55                  60

Glu Gly Val Pro Met Ile Phe Ser Asp Phe Gly Leu Asp Gln Pro Leu
65                  70                  75                  80

Asn Ala Arg Tyr Met Ser Asp Val Leu Lys Val Gly Val Tyr Leu Glu
                85                  90                  95

Asn Gly Trp Glu Arg Gly Glu Ile Ala Asn Ala Ile Arg Arg Leu Met
            100                 105                 110

Val Asp Glu Glu Gly Glu Tyr Ile Arg Gln Asn Ala Arg Val Leu Lys
        115                 120                 125

Gln Lys Ala Asp Val Ser Leu Met Lys Gly Gly Ser Ser Tyr Glu Ser
    130                 135                 140

Leu Glu Ser Leu Val Ser Tyr Ile Ser Ser Leu Gly Ser Gly Gly Ser
145                 150                 155                 160

Gly Gly Ser Gly Arg Arg Arg Ile Ile Leu Phe Pro Val Pro Phe
                165                 170                 175

Gln Gly His Ile Asn Pro Met Leu Gln Leu Ala Asn Val Leu Tyr Ser
            180                 185                 190

Lys Gly Phe Ser Ile Thr Ile Phe His Thr Asn Phe Asn Lys Pro Lys
        195                 200                 205

Thr Ser Asn Tyr Pro His Phe Thr Phe Arg Phe Ile Leu Asp Asn Asp
    210                 215                 220

Pro Gln Asp Glu Arg Ile Ser Asn Leu Pro Thr His Gly Pro Leu Ala
225                 230                 235                 240

Gly Met Arg Ile Pro Ile Ile Asn Glu His Gly Ala Asp Glu Leu Arg
                245                 250                 255

Arg Glu Leu Glu Leu Leu Met Leu Ala Ser Glu Glu Asp Glu Glu Val
            260                 265                 270

Ser Cys Leu Ile Thr Asp Ala Leu Trp Tyr Phe Ala Gln Ser Val Ala
        275                 280                 285

Asp Ser Leu Asn Leu Arg Arg Leu Val Leu Met Thr Ser Ser Leu Phe
    290                 295                 300

Asn Phe His Ala His Val Ser Leu Pro Gln Phe Asp Glu Leu Gly Tyr
305                 310                 315                 320

Leu Asp Pro Asp Asp Lys Thr Arg Leu Glu Glu Gln Ala Ser Gly Phe
                325                 330                 335

Pro Met Leu Lys Val Lys Asp Ile Lys Ser Ala Tyr Ser Asn Trp Gln
            340                 345                 350
```

```
Ile Ala Lys Glu Ile Leu Gly Lys Met Ile Lys Gln Thr Lys Ala Ser
            355                 360                 365

Ser Gly Val Ile Trp Asn Ser Phe Lys Glu Leu Glu Ser Glu Leu
    370                 375                 380

Glu Thr Val Ile Arg Glu Ile Pro Ala Pro Ser Phe Leu Ile Pro Leu
385                 390                 395                 400

Pro Lys His Leu Thr Ala Ser Ser Ser Leu Leu Asp His Asp Arg
                405                 410                 415

Thr Val Phe Gln Trp Leu Asp Gln Gln Pro Ser Ser Val Leu Tyr
                420                 425                 430

Val Ser Phe Gly Ser Thr Ser Glu Val Asp Glu Lys Asp Phe Leu Glu
            435                 440                 445

Ile Ala Arg Gly Leu Val Asp Ser Gln Ser
            450                 455

<210> SEQ ID NO 6
<211> LENGTH: 455
<212> TYPE: PRT
<213> ORGANISM: Stevia rebaudiana

<400> SEQUENCE: 6

Met Ala Phe Leu Trp Val Val Arg Pro Gly Phe Val Lys Gly Ser Thr
1               5                   10                  15

Trp Val Glu Pro Leu Pro Asp Gly Phe Leu Gly Glu Arg Gly Arg Ile
            20                  25                  30

Val Lys Trp Val Pro Gln Gln Glu Val Leu Ala His Gly Ala Ile Gly
        35                  40                  45

Ala Phe Trp Thr His Gly Gly Trp Asn Ser Thr Leu Glu Ser Val Cys
    50                  55                  60

Glu Gly Val Pro Met Ile Phe Ser Asp Phe Gly Leu Asp Gln Pro Leu
65                  70                  75                  80

Asn Ala Arg Tyr Met Ser Asp Val Leu Lys Val Gly Val Tyr Leu Glu
                85                  90                  95

Asn Gly Trp Glu Arg Gly Glu Ile Ala Asn Ala Ile Arg Arg Leu Met
            100                 105                 110

Val Asp Glu Glu Gly Glu Tyr Ile Arg Gln Asn Ala Arg Val Leu Lys
        115                 120                 125

Gln Lys Ala Asp Val Ser Leu Met Lys Gly Gly Ser Ser Tyr Glu Ser
    130                 135                 140

Leu Glu Ser Leu Val Ser Tyr Ile Ser Ser Leu Gly Ser Gly Gly Ser
145                 150                 155                 160

Gly Arg Arg Arg Arg Ile Ile Leu Phe Pro Val Pro Phe Gln Gly His
                165                 170                 175

Ile Asn Pro Met Leu Gln Leu Ala Asn Val Leu Tyr Ser Lys Gly Phe
            180                 185                 190

Ser Ile Thr Ile Phe His Thr Asn Phe Asn Lys Pro Lys Thr Ser Asn
        195                 200                 205

Tyr Pro His Phe Thr Phe Arg Phe Ile Leu Asp Asn Asp Pro Gln Asp
    210                 215                 220

Glu Arg Ile Ser Asn Leu Pro Thr His Gly Pro Leu Ala Gly Met Arg
225                 230                 235                 240

Ile Pro Ile Ile Asn Glu His Gly Ala Asp Glu Leu Arg Arg Glu Leu
                245                 250                 255

Glu Leu Gln Met Leu Ala Ser Glu Glu Asp Glu Glu Val Ser Cys Leu
```

```
                    260                 265                 270
Ile Thr Asp Ala Leu Trp Tyr Phe Ala Gln Ser Val Ala Asp Ser Leu
            275                 280                 285

Asn Leu Pro Arg Leu Val Leu Met Thr Ser Ser Leu Phe Asn Phe His
        290                 295                 300

Ala His Val Ser Leu Pro Gln Phe Asp Glu Leu Gly Tyr Leu Asp Pro
305                 310                 315                 320

Asp Asp Lys Thr Arg Leu Glu Glu Gln Ala Ser Gly Phe Pro Met Leu
                325                 330                 335

Lys Val Lys Asp Ile Lys Ser Ala Tyr Ser Asn Trp Gln Ile Ala Lys
            340                 345                 350

Glu Ile Leu Gly Lys Met Ile Lys Gln Thr Lys Ala Ser Ser Gly Val
        355                 360                 365

Ile Trp Asn Ser Phe Lys Glu Leu Glu Ser Glu Leu Glu Thr Val
                370                 375                 380

Ile Arg Glu Ile Pro Ala Pro Ser Phe Leu Ile Pro Leu Pro Lys His
385                 390                 395                 400

Leu Thr Ala Ser Ser Ser Leu Leu Glu His Asp Arg Thr Val Phe
                405                 410                 415

Gln Trp Leu Asp Gln Gln Pro Pro Ser Ser Val Leu Tyr Val Ser Phe
            420                 425                 430

Gly Ser Thr Ser Glu Val Asp Glu Lys Asp Phe Leu Glu Ile Ala Arg
        435                 440                 445

Gly Leu Val Asp Ser Gln Ser
    450                 455

<210> SEQ ID NO 7
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 7

Gly Ser Gly Gly Ser Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 8

Gly Ser Gly Gly Ser Gly Gly Ser Gly
1               5

<210> SEQ ID NO 9
<211> LENGTH: 447
<212> TYPE: PRT
<213> ORGANISM: Stevia rebaudiana

<400> SEQUENCE: 9

Met Ala Phe Leu Trp Val Arg Pro Gly Phe Val Lys Gly Ser Thr
1               5                   10                  15

Trp Val Glu Pro Leu Pro Asp Gly Phe Leu Gly Glu Arg Gly Arg Ile
            20                  25                  30

Val Lys Trp Val Pro Gln Gln Glu Val Leu Ala His Gly Ala Ile Gly
```

```
                35                  40                  45
Ala Phe Trp Thr His Gly Gly Trp Asn Ser Thr Leu Glu Ser Val Cys
 50                  55                  60

Glu Gly Val Pro Met Ile Phe Gln Asp Phe Gly Leu Asp Gln Pro Leu
 65                  70                  75                  80

Asn Ala Arg Tyr Met Ser Asp Val Leu Lys Val Gly Val Tyr Leu Glu
                 85                  90                  95

Asn Gly Trp Glu Arg Gly Glu Ile Ala Asn Ala Ile Arg Arg Leu Met
                100                 105                 110

Val Asp Glu Glu Gly Glu Tyr Ile Arg Gln Asn Ala Arg Val Leu Lys
                115                 120                 125

Gln Lys Ala Asp Val Ser Leu Met Lys Gly Gly Ser Ser Tyr Glu Ser
130                 135                 140

Leu Glu Ser Leu Val Ser Tyr Ile Ser Ser Leu Gly Ser Gly Gly Ser
145                 150                 155                 160

Gly Arg Arg Arg Arg Ile Ile Leu Phe Pro Val Pro Phe Gln Gly His
                165                 170                 175

Ile Asn Pro Met Leu Gln Leu Ala Asn Val Leu Tyr Ser Lys Gly Phe
                180                 185                 190

Ser Ile Thr Ile Phe His Thr Asn Phe Asn Lys Pro Lys Thr Ser Asn
                195                 200                 205

Tyr Pro His Phe Thr Phe Arg Phe Ile Leu Asp Asn Asp Pro Gln Asp
                210                 215                 220

His Gly Pro Leu Ala Gly Met Arg Ile Pro Ile Ile Asn Glu His Gly
225                 230                 235                 240

Ala Asp Glu Leu Arg Arg Glu Leu Glu Leu Gln Met Leu Ala Ser Glu
                245                 250                 255

Glu Asp Glu Glu Val Ser Cys Leu Ile Thr Asp Ala Leu Trp Tyr Phe
                260                 265                 270

Ala Gln Ser Val Ala Asp Ser Leu Asn Leu Pro Arg Leu Val Leu Met
                275                 280                 285

Thr Ser Ser Leu Phe Asn Phe His Cys His Val Ser Leu Pro Gln Phe
290                 295                 300

Asp Glu Leu Gly Tyr Leu Asp Pro Asp Asp Lys Thr Arg Leu Glu Glu
305                 310                 315                 320

Gln Ala Ser Gly Phe Pro Met Leu Lys Val Lys Asp Ile Lys Ser Ala
                325                 330                 335

Phe Ser Asn Trp Gln Ile Ala Lys Glu Ile Leu Gly Lys Met Ile Lys
                340                 345                 350

Gln Thr Lys Ala Ser Ser Gly Val Ile Trp Asn Ser Phe Lys Glu Leu
                355                 360                 365

Glu Glu Ser Glu Leu Glu Thr Val Ile Arg Glu Ile Pro Ala Pro Ser
370                 375                 380

Phe Leu Ile Pro Leu Pro Lys His Leu Thr Ala Ser Ser Ser Ser Leu
385                 390                 395                 400

Leu Glu His Asp Arg Thr Val Phe Gln Trp Leu Asp Gln Gln Pro Pro
                405                 410                 415

Ser Ser Val Ile Tyr Val Ser Phe Gly Ser Thr Ser Glu Val Asp Glu
                420                 425                 430

Lys Asp Phe Leu Glu Ile Ala Arg Gly Leu Val Asp Ser Gln Ser
                435                 440                 445
```